(12) United States Patent
Kasprzak

(10) Patent No.: US 11,080,893 B2
(45) Date of Patent: Aug. 3, 2021

(54) ANALYSIS UNIT AND SYSTEM FOR ASSESSMENT OF HAIR CONDITION

(71) Applicant: Michal Pawel Kasprzak, Falenty Duze (PL)

(72) Inventor: Michal Pawel Kasprzak, Falenty Duze (PL)

(*) Notice: Subject to any disclaimer, the term of this patent is extended or adjusted under 35 U.S.C. 154(b) by 0 days.

(21) Appl. No.: 16/744,049

(22) Filed: Jan. 15, 2020

(65) Prior Publication Data

US 2020/0202565 A1 Jun. 25, 2020

Related U.S. Application Data

(63) Continuation of application No. 15/675,117, filed on Aug. 11, 2017, now Pat. No. 10,573,026.

(30) Foreign Application Priority Data

Dec. 29, 2016 (PL) .......................................... 420023

(51) Int. Cl.
*G06K 9/00* (2006.01)
*G06T 7/77* (2017.01)
(Continued)

(52) U.S. Cl.
CPC .............. *G06T 7/77* (2017.01); *A61B 5/0077* (2013.01); *A61B 5/1072* (2013.01); *A61B 5/446* (2013.01); *A61B 5/448* (2013.01); *A61B 5/7282* (2013.01); *G06T 7/0012* (2013.01); *G06T 7/90* (2017.01); *A45D 2044/007* (2013.01);
(Continued)

(58) Field of Classification Search
CPC .......... A45D 2044/007; A61B 2576/02; A61B 5/0066; A61B 5/0077; A61B 5/1072; A61B 5/446; A61B 5/448; A61B 5/7282; G06T 2207/10024; G06T 2207/10056;
(Continued)

(56) References Cited

U.S. PATENT DOCUMENTS 5,331,472 A 7/1994 Rassman
7,962,192 B2 6/2011 Bodduluri et al.
(Continued)

OTHER PUBLICATIONS

Ross, et al., 'Videodermoscopy in the evaluation of hair and scalp disorders', Nov. 2006;55(5):799-806. Epub, Jul. 31, 2006.
(Continued)

*Primary Examiner* — Xin Jia
(74) *Attorney, Agent, or Firm* — Kenealy Vaidya LLP

(57) ABSTRACT

Some embodiments are directed to an analysis unit for assessment of hair condition, including a map processor configured to at least: obtain a first follicular map representing a first plurality of hair root positions in a first videodermoscopy image, obtain a second follicular map representing a second plurality of hair root positions in a second videodermoscopy image, determine a common skin area from the first follicular map and the second follicular map, relate hair root positions in the second follicular map to hair root positions of the first follicular map in the common skin area to determine a plurality of related hair root positions, and compare a change in condition of individual hair between the first and second videodermoscopy image to determine the analysis result suitable for assessment of hair condition.

20 Claims, 17 Drawing Sheets

(51) Int. Cl.
  *A61B 5/00* (2006.01)
  *A61B 5/107* (2006.01)
  *G06T 7/90* (2017.01)
  *G06T 7/00* (2017.01)
  *A45D 44/00* (2006.01)

(52) U.S. Cl.
  CPC ......... *A61B 5/0066* (2013.01); *A61B 2576/02* (2013.01); *G06T 2207/10024* (2013.01); *G06T 2207/10056* (2013.01); *G06T 2207/30088* (2013.01)

(58) Field of Classification Search
  CPC ......... G06T 2207/30088; G06T 7/0012; G06T 7/77; G06T 7/90
  See application file for complete search history.

(56) References Cited

U.S. PATENT DOCUMENTS

| | | | |
|---|---|---|---|
| 8,809,014 B2 | 8/2014 | Kosaga et al. | |
| 8,941,727 B2 | 1/2015 | Rassman et al. | |
| 2004/0201694 A1 | 10/2004 | Garstein et al. | |
| 2008/0049992 A1 | 2/2008 | Qureshi et al. | |
| 2008/0216334 A1 | 9/2008 | Pak et al. | |
| 2009/0036800 A1 | 2/2009 | Rabin et al. | |
| 2009/0248748 A1* | 10/2009 | Shahmoradian | A45D 44/005 |
| 2010/0262129 A1* | 10/2010 | Roy | A61B 90/30 606/10 |
| 2012/0230561 A1* | 9/2012 | Qureshi | G06T 7/0012 382/128 |
| 2012/0250958 A1 | 10/2012 | Kang | |
| 2013/0190776 A1 | 7/2013 | Zhang et al. | |
| 2014/0028822 A1 | 1/2014 | Khadavi et al. | |
| 2015/0112204 A1 | 4/2015 | Bodduluri et al. | |
| 2016/0253799 A1* | 9/2016 | Rahman | G06K 9/6218 382/128 |
| 2016/0307333 A1 | 10/2016 | Qureshi et al. | |
| 2016/0324586 A1* | 11/2016 | Zingaretti | A61B 5/4836 |
| 2017/0032223 A1 | 2/2017 | Lingaretti et al. | |
| 2017/0333432 A1 | 11/2017 | Sinclair | |

OTHER PUBLICATIONS

IQ Hair: "Trichoscopy, Always the first step against hair loss", May 6, 2016 (May 6, 2016), XP055447171, Retrieved from the Internet: URL:https',llweb.archive.org/web12016050615211 lhTTp://iqhair.com:80/en/trichoscopy.

Jun. 4, 2018 U.S. Office Action issued in U.S. Appl. No. 15/418,549.

Rakowska et al., "Trichoscopy in genetic hair shaft abnormalities", Journal of Dermatological Case Reports, vol. 2008, No. 2, Oct. 2008, pp. 14-20.

Rakowska et al., "Trichoscopic Hair Evaluation in Patients with Ectodermal Dysplasia", Journal of Pediatrics, vol. 167, No. 1, Apr. 2015, pp. 193-195.

Vujovic et al., "The Female Pattern Hair Loss: Review of Etiopathogenesis and Diagnosis", BioMed Research International, vol. 2014, Oct. 2014, pp. 1-9.

Dhurat et al., "Hair Evaluation Methods: Merits and Demerits", International Journal of Trichology, Jul.-Dec. 2009; 1(2): 28 pages.

S. Bielfeldt, et al., "Use of image analysis techniques for objective quantification of the efficacy of different hair removal methods", Journal of Cosmetic Science, 57, pp. 345-354 (Sep./Oct. 2006).

* cited by examiner

ANALYSIS UNIT AND SYSTEM FOR ASSESSMENT OF HAIR CONDITION

CROSS REFERENCE TO RELATED APPLICATION

This application is a continuation application of U.S. patent Applicant Ser. No. 15/675,117 filed on Aug. 11, 2017, which claims benefit of Polish Priority Patent Application P.420023 filed Dec. 29, 2016, the entire contents of each of which are incorporated herein by reference in their entireties.

FIELD

The invention relates to an analysis unit for assessment of hair condition, a system for assessment of hair condition, a method for assessment of hair condition, and a computer program product.

BACKGROUND ART

Hair condition, in particular hair disorders, have traditionally been assessed by clinical inspection and a number of invasive methods including a pull-test, a trichogram obtained from extraction of approximately hundred hairs for microscopic inspection of their roots, and patomorphology which uses biopsy after extraction of skin tissue for microscopic inspection.

In 2006, it was proposed by Ross, E K, Vincenzi, C I, and Tosti, A. that a dermoscope or videodermoscope, traditionally used for skin lesion observations, may be used for diagnosing hair disorders. Since then their method, usually referred to as trichoscopy, has gained some popularity due to its non-invasiveness. A number of studies have been carried out to provide guidelines for disease diagnosis based on visual, qualitative inspection of the videodermosopy images by a trained dermatologist doctor. Visual trichoscopy has generally focused on setting the initial diagnosis based on certain characteristic features observed in the dermoscopy images of the scalp, such as broken hair, yellow dots, black dots, tulip hair, arborizing vessels, etc. This qualitative inspection of the videodermosopy images did not provide tools to, for example, clearly distinguish between most common conditions like to distinguish Androgenetic alopecia (AGA) from diffuse Alopecia areata (AA) and Telogen effluvium (TE), precisely measure advancement of AGA, or to precisely measure therapy efficiency once medication is introduced.

The term trichoscopy may further be used to refer to a technique used in the assessment of hair condition, examination of symptoms of hair disorder, diagnosis of hair disorders, and monitoring hair treatment efficiency. Trichoscopy uses a microscopic camera, a so-called videodermoscope to register high resolution images of hair and scalp or other skin. Such images may further be referred to as videodermoscopy images. In known methods, the videodermoscopy images are subject to manual or computer-assisted analysis to try to identify all hair shafts and measure hair diameters. A statistical analysis of images registered before and after the treatment allows to assess the response to treatment in terms of, for example, hair number or hair density, hair thickness and hair volume. In order to try to detect therapeutic effects in the pre- and post-image comparison, a multiple micro tattoo marking is used to help to identify the same skin location and field of view, with the aim of positioning the videodermoscope at the same position after the treatment as before. Known methods suffer from various limitations. For example, it may be difficult or even impossible to draw any conclusions if the overall hair density change is statistically insignificant. Also, currently used methods do not allow to ensure that the pre- and post-images represent really the same skin area. Further, with known methods, the precision of the analysis relies strongly on exactly the same positioning of the camera on the skin and the same field of view.

Known trichoscopy techniques used in the assessment of hair condition, examination of symptoms of hair disorder, diagnosis of hair disorders and monitoring hair treatment efficiency thus still suffer from various limitations.

SUMMARY

A first aspect of the invention provides an analysis unit for assessment of hair condition, the analysis unit comprising a map processor, the map processor being arranged to at least obtain a first follicular map representing a first plurality of hair root positions in a first videodermoscopy image, and analyse at least the first follicular map to determine an analysis result suitable for assessment of hair condition. Assessment of hair condition may comprise supporting examination of symptoms of hair disorder, supporting examination of symptoms of skin disorder, supporting diagnosis of hair disorder, supporting diagnosis of skin disorder, supporting examination of treatment, supporting examination of a change in hair condition, or supporting examination and/or evaluation of treatment efficiency. The analysis result suitable for assessment of hair condition may relate to, consist of or comprise a parameter known and used in triochoscopy such as hair density. The analysis result suitable for assessment of hair condition may relate to, consist of or comprise any other analysis result for assessment hair condition, such as, for example, one of the analysis results described with reference to embodiments below, for example being indicative of AGA. The analysis unit may be arranged to support diagnosis of hair disorder. The analysis unit may additionally or alternatively be arranged to support examination and/or evaluation of treatment efficiency. The analysis unit may be used in trichoscopy to assess hair condition. Using the first follicular map representing the first plurality of hair root positions as an alternative of using a corresponding first videodermoscopy image, or in addition to using the corresponding first videodermoscopy image, may provide an analysis result that is better suitable for assessment of hair condition according to known methods. The analysis result may, for example, comprise a known type of analysis result, such as hair density, that is more accurately determined than at least some known methods. The analysis result may, additionally or alternatively, comprise a new type of result that is better suitable than known types as, for example, a result indicative of a degree of AGA. Examples are described below with reference to various embodiments. The analysis unit may be arranged to analyse a plurality of follicular maps, the plurality of follicular maps comprising the first follicular map, to determine an analysis result suitable for assessment of hair condition. The analysis unit may be arranged to analyse at least the first follicular map and a corresponding first videodermoscopy image, to determine an analysis result suitable for assessment of hair condition. The various embodiments described below may be used autonomously or in combination of one or more embodiments. The embodiments described may overcome, reduce or alleviate various limitations of known trichoscopy techniques. The specific limitation or limitations that are overcome, reduced or alleviated by a specific embodiment may be different for the different embodiments and any combinations thereof.

In an embodiment, the analysis unit further comprises an image processor, the image processor being arranged to perform an image processing algorithm on a first videodermoscopy image to generate the first follicular map representing the first plurality of hair root positions in the first videodermoscopy image, and the map processor being arranged to obtain the first follicular map from the image processor.

In an embodiment, the image processor is arranged to, as part of obtaining the first follicular map, cooperate with a map modification unit, the map modification unit being arranged to present the first follicular map as obtained from the performing of the image processing algorithm on the first videodermoscopy image to a human assistant, and allow the human assistant to review the first follicular map and to modify the first follicular map such as to, at least, add and/or remove one or more hair root positions from the first follicular map.

In an embodiment, the map processor is arranged to, as part of analysing at least the first follicular map to determine the analysis result, perform a statistical analysis of hair root distances between hair roots positions of the first plurality of hair root positions.

In an embodiment, the map processor is arranged to, as part of performing the statistical analysis of hair root distances between hair root positions, determine a hair root distance distribution, and determine at least a first and a second relative contribution to the hair root distance distribution of at least a first and a second distribution component function.

In an embodiment, the relative contribution of the first distribution component function is an indication for a degree of a hair disorder of a first type. For example, the relative contribution of the first distribution component function is an indication for a degree of AGA.

In an embodiment, the map processor is further arranged to at least obtain a second follicular map representing a second plurality of hair root positions in a second videodermoscopy image, and determine a common skin area from the first follicular map and the second follicular map. The map processor may further be arranged to use the common skin area in analysing at least the first follicular map to determine the analysis result suitable for assessment of hair condition. The map processor may be arranged to use the common skin area in analysing at least the first and the second follicular map to determine the analysis result suitable for assessment of hair condition. For example, comparing the common skin area of a first follicular map obtained from a first videodermoscopy image recorded at a first moment in time with the common skin area of the second follicular map obtained from a second videodermoscopy image recorded at a second, later, moment in time may provide an analysis result that is better suitable for assessment of hair condition than known methods, such as for assessment of a change in hair condition between the first moment and the second moment, for example as result of a treatment. For example, the analysis result may comprise a change in hair density and/or a change in number of hair and/or identification of appeared and disappeared hair, which may be more accurately obtained using the common skin area than from a mere comparison of the first and second videodermoscopy images or the corresponding hair densities determined therefrom. Other examples are described below with reference to various embodiments.

In an embodiment, the map processor is further arranged to obtain a sequence of second follicular maps, each second follicular map representing a second plurality of hair root positions in an associated second videodermoscopy image of a corresponding sequence of different second videodermoscopy images, and determine a common skin area from the first follicular map and at least one of the second follicular maps of the sequence of second follicular maps. Thus, the sequence of second videodermoscopy images may be acquired from the person's skin without the need to know the exact location and without the need for additional reference symbols such as, e.g., micro-tattoos: the first follicular map effectively acts as the location reference, and could be considered to function as a virtual tattoo. With this embodiment, the system may not just be arranged for determining an analysis result suitable for assessment of hair condition, but the system may additionally or alternatively be arranged for determining an analysis result suitable for assessment of skin condition. Herein, the follicular maps may be used to determine a corresponding skin area when a skin condition, and particularly a change in skin condition, is to be assessed. The skin condition may e.g. relate to detecting, measuring or monitoring skin color, skin color variation, presence and growth of birthmarks, naevus, scars, skin burn, skin recovery, and their development over time.

In an embodiment, the image processor is further arranged to perform an image processing algorithm on a second videodermoscopy image to generate the second follicular map representing the second plurality of hair root positions in the second videodermoscopy image, and the map processor is arranged to obtain the second follicular map from the image processor.

In an embodiment, the map processor comprises a matching unit, the matching unit being arranged to at least relate hair root positions in the second follicular map to hair root positions of the first follicular map in the common skin area to determine a plurality of related hair root positions, each related hair root position of a hair root in the second follicular map being related to a hair root position in the first follicular map of the same hair root. A related hair root position of a hair root in the second follicular map may hereby be related to a hair root position in the first follicular map of the same hair root representing presumably the same hair follicle in the second and first videodermoscopy images. The map processor may further be arranged to compare a change in condition of individual hair between the first and second videodermoscopy image to determine the analysis result suitable for assessment of hair condition.

In an embodiment, the matching unit is arranged to initialize a transformation function, and to iteratively adapt the transformation function, the iterative adaption comprising applying the transformation function to the first plurality of hair root positions of the first follicular map to obtain a first plurality of transformed hair root positions, relating the first plurality of transformed hair root positions to the second plurality of hair root positions of the second follicular map, determining relative distances between transformed hair root positions of the first plurality of transformed hair root positions and the related hair root positions of the second plurality of hair root positions to obtain a correspondence metric, and adapting the transformation function to minimize the correspondence metric.

In an embodiment, the matching unit is arranged to, as part of iteratively adapting the transformation function, further use at least one parameter of hair associated with the transformed hair root positions and hair associated with the related hair root positions to obtain the correspondence metric, the at least one parameter comprising at least one parameter from a group consisting of hair shaft diameter, hair length, hair growth, hair color.

In an embodiment, the matching unit is arranged to, as part of initializing the transformation function, detect positions of a first plurality of reference symbols on the skin in the first videodermoscopy image, detect positions of a second plurality of reference symbols on the skin in the second videodermoscopy image, and initialize the transformation function to reflect a transformation from the positions of a first plurality of reference symbols to the positions of a second plurality of reference symbols. In an embodiment, the map processor is further arranged to at least analyse differences between at least the common skin area in the first follicular map and the common skin area in the second follicular map to determine the analysis result suitable for assessment of hair condition.

In an embodiment, the map processor is further arranged to, in determining the analysis result, identify an appearing of new hair shafts in the common skin area in the second follicular map compared to the common skin area in the first follicular map.

In an embodiment, the map processor is further arranged to, in determining the analysis result, identify a disappearing of hair from the common skin area in the second follicular map compared to the common skin area in the first follicular map.

In an embodiment, the map processor is further arranged to at least analyse differences between at least the common skin area in the first videodermoscopy image and the common skin area in the second videodermoscopy image to determine the analysis result suitable for assessment of hair condition.

In an embodiment, the map processor is further arranged to, in analysing differences between at least the common skin area in the first videodermoscopy image and the common skin area in the second videodermoscopy image, determine differences between at least one parameters of a group of parameters consisting of average hair diameter, hair diameter distribution, average hair length, hair length distribution, hair colors, hair color distribution, and/or at least one hair density.

The hair condition may thus comprise or relate to hair length or change of hair length. Comparing a change in condition may comprise or correspond to comparing lengths of individual hairs in the first and second videodermoscopy images to determine a length increase, usually growth, or a length reduction, e.g. from shaving or cutting.

In an embodiment, the map processor is further arranged to, in analysing differences between at least the common skin area in the first videodermoscopy image and the common skin area in the second videodermoscopy image, compare lengths of individual hair between the first videodermoscopy image captured from a part of a skin, such as part of a human scalp, before shaving and lengths of the same individual hair in a second videodermoscopy image captured from the same part after shaving as part of an examination of shaving performance on hair condition, in particular hair length. Hereby, an analysis result suitable for the assessment of hair condition may be obtained which is indicative for the shaving performance.

In an embodiment, the map processor is further arranged to, in analysing differences between at least the common skin area in the first videodermoscopy image and the common skin area in the second videodermoscopy image, compare lengths of individual hairs between a first videodermoscopy image captured from a part of a skin, such as part of a human scalp, immediately after shaving and a second videodermoscopy image captured from the same part one or more days after shaving, and to calculate estimates of the lengths of individual hairs immediately after shaving from the change of lengths. Hereby, it becomes possible to also assess the quality of shaving, such as of close shaving that uses a razor blade arranged to pull hair out and cut the hair effectively below skin surface: the estimates may then provide negative lengths of individual hairs as a result of the shaving. The analysis result suitable for assessment of hair condition may thus be a set of lengths, which may include negative lengths, of individual hairs reflecting the hair condition immediately after shaving, or one or more statistical parameters measured on the set of negative lengths of individual hair reflecting statistical performance indicators of the hair condition after shaving, such as an average (possible negative) length. The part of a skin may, e.g., be a part of a human skin such as a part of a human scalp, face, or another body part.

In an embodiment, the map processor is further arranged to, in analysing differences between at least the common skin area in the first videodermoscopy image and the common skin area in the second videodermoscopy image, compare presence and/or diameters and/or lengths of individual hair between the first videodermoscopy image captured from a part of a skin before epilation and presence and/or diameters and/or lengths of the same individual hair in a second videodermoscopy image captured from the same part after epilation as part of an examination of epilation performance on hair condition, in particular hair extraction, hair diameter and hair length. Hereby, an analysis result suitable for the assessment of hair condition may be obtained which is indicative for the epilation performance. The assessment of epilation builds in part on the recognition that the available techniques for epilation, such as mechanical, electrocoagulation and laser epilation, aim at hurting the hair follicle without too much skin damage: epilation will thus in practice never lead to a 100% extraction of all hair from the hair follicles. Further, the inventors recognized that hair cycling causes a certain fraction X % of hair follicles to be in the telogen/exogen phase thus to be "empty". As a result, after one depilation session there is always some hair regrowth due to follicles that got hurt but not destroyed—these hairs will be thinner and grow slower- and due to the remaining X % of follicles that were not detected and not affected at all. This embodiment provides estimates of the positions of hair follicles and the correspondence between hair follicle locations between the first and second follicular maps, which allows to evaluate the remaining hair and to tell one effect from another.

In an embodiment, the map processor is further arranged to, in analysing differences between at least the common skin area in the first videodermoscopy image and the common skin area in the second videodermoscopy image, compare presence and/or diameters and/or lengths of individual hair between a first videodermoscopy image captured from a part of a skin immediately or shortly after epilation and a second videodermoscopy image captured from the same part one or more days after epilation, and to calculate estimates of the quality of epilation such as percentage of successful epilation and/or diameter and/or lengths of individual hair immediately after epilation from the change of diameters and/or lengths. Hereby, it becomes possible to also assess the quality of epilation, including the effect of pulling hair out and the damage to the hair follicles. The latter result in some hair regrowth due to follicles that got hurt but not destroyed—these hair will be thinner and grow slower. The analysis result suitable for assessment of hair condition may thus comprise a set of quantitative measures of efficiency of epilation, a set of diameters, a set of lengths of individual hairs reflecting the hair condition immediately after epilation, one or more statistical parameters measured on the regrowth of individual hair, and/or an indicator indicative for the damage to hair follicles derived from a statistical analysis of increase in diameters and lengths of individual hairs.

In an embodiment, the analysis unit comprises a zero-loss processor, the zero-loss processor comprising an input image processor, a matching unit, and a follicular map combiner and/or an input image combiner, the zero-loss processor being arranged to receive a plurality of first videodermoscopy input images, the input image processor being arranged to perform an image processing algorithm on each of the first videodermoscopy input images of the plurality of first videodermoscopy input images to generate a plurality of first follicular maps, each first follicular map representing a first plurality of hair root positions in the corresponding first videodermoscopy input image, the matching unit being arranged to at least relate hair root positions in a second map of the plurality of first follicular maps to hair root positions of a first map in at least a common skin area of the first map and the second map to determine a plurality of related hair root positions, the follicular map combiner being arranged to determine a combined first follicular map from the plurality of first follicular maps, the input image combiner being arranged to determine a combined input image from plurality of first videodermoscopy input images using the plurality of first follicular maps. The plurality of first videodermoscopy input images may have been captured as a sequence of videodermoscopy images while rearranging the camera used for capturing the videodermoscopy images and/or the hair in between successive images. The plurality of first videodermoscopy input images may e.g. have been captured as a sequence of videodermoscopy images taken shortly after each other, such as at intervals in a range of 10 ms to 10 minutes, such as at intervals in a range of 10 ms to 50 ms, 0.5 sec to 30 sec, 1 to 5 minutes, or any other suitable interval. The plurality of first videodermoscopy input images may e.g. have been captured using a digital still camera to provide a sequence of still images as the sequence of videodermoscopy images. The plurality of first videodermoscopy input images may e.g. have been captured using a video camera to provide a sequence of video frames as the sequence of videodermoscopy images. The sequence of video frames may for example have been captured at a frame rate in a range of 10 to 100 Hz, such as at a frame rate of 16, 25, 50, 60, 75 or 100 Hz, or any other suitable frame rate. The sequence of videodermoscopy images may correspond to a series of successive video frames. The sequence of videodermoscopy images may correspond to a subsampled series of video frames, such as every second, every third, every fifth or every tenth video frame of a series of successive video frames, or any other suitable subsampling rate. The plurality of first videodermoscopy input images may e.g. have been captured while reorganizing the hair, such as by combing the hair, parting the hair, wetting the hair or any other suitable manner in between successive videodermoscopy images. The plurality of first videodermoscopy input images may e.g. have been captured while shifting or rotating the camera in between successive videodermoscopy images, or varying the imaging distance or magnification.

In an embodiment, the zero-loss processor is arranged to output the combined first follicular map to the image processor, for use as the first or second follicular map in any one of the embodiments described above.

In an embodiment, the zero-loss processor is arranged to output the combined input image to the image processor for use as the first or second videodermoscopy image in any one of the embodiments described above.

A second aspect of the invention provides a system for assessment of hair condition, the system comprising an upload unit, an analysis unit according to any one of the preceding embodiments, and a presentation unit, the upload unit being arranged to receive one or more videodermoscopy images, the one or more videodermoscopy images comprising at least the first videodermoscopy image and to upload the one or more videodermoscopy images to the analysis unit, the analysis unit being arranged to receive the one or more videodermoscopy images from the upload unit and to obtain a videodermoscopic analysis result from the one or more videodermoscopy images, the videodermoscopic analysis result comprising the analysis result suitable for assessment of hair condition and/or an examination result derived from the analysis result, and the presentation unit being arranged to receive the videodermoscopic analysis result from the analysis unit and to present at least part of the analysis result to a user.

In an embodiment, the system further comprising a result check unit, the result check unit being arranged to receive the videodermoscopic analysis result from the analysis unit, review the videodermoscopic analysis result and to modify the videodermoscopic analysis result, provide the videodermoscopic analysis result as modified to the presentation unit to allow the presentation unit to present at least part of the videodermoscopic analysis result as modified to the user.

In an embodiment, the upload unit is connected to the analysis unit via a communication network.

In an embodiment, the presentation unit is connected to the analysis unit via a communication network.

In an embodiment, the system further comprises a user terminal, the user terminal comprising the upload unit and the presentation unit, the user terminal being connected to the analysis unit via a communication network.

A third aspect of the invention provides a method for assessment of hair condition, the method comprising obtaining a first follicular map representing a first plurality of hair root positions in a first videodermoscopy image, and analysing at least the first follicular map to determine an analysis result suitable for assessment of hair condition.

In an embodiment, the method further comprises performing an image processing algorithm on a first videodermoscopy image to obtain the first follicular map representing the first plurality of hair root positions in the first videodermoscopy image.

In an embodiment, the method further comprises obtaining a second follicular map representing a second plurality of hair root positions in a second videodermoscopy image, and determining a common skin area from the first follicular map and the second follicular map.

In an embodiment, the method further comprises performing an image processing algorithm on a second videodermoscopy image to obtain the second follicular map representing the second plurality of hair root positions in the second videodermoscopy image.

In an embodiment, the method comprises obtaining a sequence of second follicular maps, each second follicular map representing a second plurality of hair root positions in an associated second videodermoscopy image of a corresponding sequence of second videodermoscopy images, and determining a common skin area from the first follicular map and at least one of the second follicular maps of the sequence of second follicular maps.

In an embodiment, the method comprises, in analysing differences between at least the common skin area in the first videodermoscopy image and the common skin area in the second videodermoscopy image, comparing lengths of individual hair between the first videodermoscopy image captured from a part of a human scalp—or another part of a skin—before shaving and lengths of the same individual hair in a second videodermoscopy image captured from the same part after shaving as part of an examination of shaving performance on hair condition, in particular hair length.

In an embodiment, the method comprises, in analysing differences between at least the common skin area in the first videodermoscopy image and the common skin area in the second videodermoscopy image, comparing lengths of individual hair between a first videodermoscopy image captured from a part of a human scalp—or another part of a skin—shortly after shaving and a second videodermoscopy image captured from the same part one or more days after shaving, and calculating estimates of the lengths of individual hair immediately after shaving from the change of lengths.

In an embodiment, the method comprises receiving a plurality of first videodermoscopy input images, performing an image processing algorithm on each of the first videodermoscopy input images of the plurality of first videodermoscopy input images to generate a plurality of first follicular maps, each first follicular map representing a first plurality of hair root positions in the corresponding first videodermoscopy input image, relating hair root positions in a second map of the plurality of first follicular maps to hair root positions of a first map in at least a common skin area of the first map and the second map to determine a plurality of related hair root positions, and determining a combined first follicular map from the plurality of first follicular maps and/or determining a combined input image from plurality of first videodermoscopy input images using the plurality of first follicular maps.

In a further embodiment, the method comprises capturing a sequence of videodermoscopy images while rearranging the camera and/or the hair in between successive images. In an embodiment, the plurality of first videodermoscopy input images is captured as a sequence of videodermoscopy images taken shortly after each other, such as at intervals between 0.1 second and 10 minutes, such as at intervals between 1 and 5 minutes. In an embodiment, the plurality of first videodermoscopy input images is captured using a digital still camera to provide a sequence of still images as the sequence of videodermoscopy images. In an embodiment, the plurality of first videodermoscopy input images is captured using a video camera to provide a sequence of video frames as the sequence of videodermoscopy images. In an embodiment, the plurality of first videodermoscopy input images is been captured while reorganizing the hair, such as by combing the hair, parting the hair, wetting the hair or any other suitable manner in between successive videodermoscopy images. In an embodiment, the plurality of first videodermoscopy input images is captured while shifting or rotating the camera in between successive videodermoscopy images, or varying the imaging distance or magnification.

In an embodiment, the method comprises uploading one or more videodermoscopy images to an analysis unit via a communication network, for letting the analysis unit perform the method according to any one of the embodiments above, and receiving the videodermoscopic analysis result from the analysis via the communication network.

In an embodiment, the method further comprises receiving one or more videodermoscopy images by an upload unit, uploading the one or more videodermoscopy images from the upload unit to an analysis unit via a communication network, for letting the analysis unit perform the method according to an embodiment, and presenting at least part of the videodermoscopic analysis result to a user.

A fourth aspect of the invention provides a computer program product comprising a computer program comprising instructions arranged to, when executed by a computer, execute at least part of the method of any one of the embodiments.

Aspects, embodiments and elements of the invention may be described by one or more of the following clauses. Further aspects, embodiments and elements may be derived from the rest of the application, such as from the rest of the summary, the brief description, the detailed description and the claims as filed. Further aspects, embodiments and elements may be derived from combining aspects, embodiments, elements and parts of aspects, embodiments, elements and parts.

Clause 1. An analysis unit for assessment of hair condition, the analysis unit comprising a map processor, the map processor being arranged to at least:
  obtain a first follicular map representing a first plurality of hair root positions in a first videodermoscopy image, and
  analyse at least the first follicular map to determine an analysis result suitable for assessment of hair condition.

Clause 2. The analysis unit according to clause 1, the analysis unit further comprising an image processor, the image processor being arranged to perform an image processing algorithm on a first videodermoscopy image to generate the first follicular map representing the first plurality of hair root positions in the first videodermoscopy image, and the map processor being arranged to obtain the first follicular map from the image processor.

Clause 3. The analysis unit according to clause 2, the image processor being arranged to, as part of obtaining the first follicular map, cooperate with a map modification unit, the map modification unit being arranged to:
  present the first follicular map as obtained from the performing of the image processing algorithm on the first videodermoscopy image to a human assistant, and
  allow the human assistant to review the first follicular map and to modify the first follicular map such as to, at least, add and/or remove one or more hair root positions from the first follicular map.

Clause 4. The analysis unit according to clause 1, the map processor being arranged to, as part of analysing at least the first follicular map to determine the analysis result, perform a statistical analysis of hair root distances between hair roots positions of the first plurality of hair root positions.

Clause 5. The analysis unit according to clause 4, the map processor being arranged to, as part of performing the statistical analysis of hair root distances between hair root positions:
  determine a hair root distance distribution, and
  determine at least a first and a second relative contribution to the hair root distance distribution of at least a first and a second distribution component function.

Clause 6. The analysis unit according to clause 5, the relative contribution of the first distribution component function being an indication for a degree of a hair disorder of a first type.

Clause 7. The analysis unit according to any one of clauses 1-3, the map processor being further arranged to at least:
obtain a second follicular map representing a second plurality of hair root positions in a second videodermoscopy image, and
determine a common skin area from the first follicular map and the second follicular map.

Clause 8. The analysis unit according to clause 7, the image processor being further arranged to perform an image processing algorithm on a second videodermoscopy image to generate the second follicular map representing the second plurality of hair root positions in the second videodermoscopy image, and
the map processor being arranged to obtain the second follicular map from the image processor.

Clause 9. The analysis unit according to clause 7 or 8, the map processor comprising a matching unit, the matching unit being arranged to at least:
relate hair root positions in the second follicular map to hair root positions of the first follicular map in the common skin area to determine a plurality of related hair root positions, each related hair root position of a hair root in the second follicular map being related to a hair root position in the first follicular map of the same hair root.

Clause 9A. An analysis unit for assessment of hair condition, the analysis unit comprising a map processor, the map processor being arranged to at least:
obtain a first follicular map representing a first plurality of hair root positions in a first videodermoscopy image,
obtain a second follicular map representing a second plurality of hair root positions in a second videodermoscopy image,
determine a common skin area from the first follicular map and the second follicular map,
relate hair root positions in the second follicular map to hair root positions of the first follicular map in the common skin area to determine a plurality of related hair root positions, each related hair root position of a hair root in the second follicular map being related to a hair root position in the first follicular map of the same hair root, and
compare a change in condition of individual hair between the first and second videodermoscopy image to determine the analysis result suitable for assessment of hair condition.

Clause 9B. The analysis unit according to clause 9A, the analysis unit further comprising an image processor,
the image processor being arranged to perform an image processing algorithm on a first videodermoscopy image to generate the first follicular map representing the first plurality of hair root positions in the first videodermoscopy image, and
the map processor being arranged to obtain the first follicular map from the image processor.

Clause 9C. The analysis unit according to clause 9B, the image processor further being arranged to perform the image processing algorithm on a second videodermoscopy image to generate the second follicular map representing the second plurality of hair root positions in the second videodermoscopy image, and
the map processor being arranged to obtain the second follicular map from the image processor.

Clause 10. The analysis unit according to any one of clauses 7-9, the map processor being further arranged to at least analyse differences between the common skin area in the first follicular map and the common skin area in the second follicular map to determine the analysis result suitable for assessment of hair condition.

Clause 11. The analysis unit according to clause 10, the map processor being further arranged to, in determining the analysis result:
identify an appearing of new hair roots in the common skin area in the second follicular map compared to the common skin area in the first follicular map, and/or
identify a disappearing of hair roots from the common skin area in the second follicular map compared to the common skin area in the first follicular map.

Clause 12. The analysis unit according to any one of clauses 7-11, the map processor being further arranged to at least analyse differences between at least the common skin area in the first videodermoscopy image and the common skin area in the second videodermoscopy image to determine the analysis result suitable for assessment of hair condition.

Clause 13. The analysis unit according to clause 12, the map processor being further arranged to, in analyse differences between at least the common skin area in the first videodermoscopy image and the common skin area in the second videodermoscopy image, determine differences between at least one parameters of a group of parameters consisting of average hair diameter, hair diameter distribution, average hair length, hair length distribution, hair colors, hair color distribution, and/or at least one hair density.

Clause 13A. The analysis unit according to any one of the preceding clauses, the analysis unit further comprising a zero-loss processor, the zero-loss processor being arranged to:
receive a plurality of first videodermoscopy input images captured as a sequence of videodermoscopy images,
perform an image processing algorithm on each of the first videodermoscopy input images of the plurality of first videodermoscopy input images to generate a plurality of first follicular maps, each first follicular map representing a first plurality of hair root positions in the corresponding first videodermoscopy input image,
relate hair root positions in a second map of the plurality of first follicular maps to hair root positions of a first map in at least a common skin area of the first map and the second map to determine a plurality of related hair root positions,
determine a combined first follicular map from the plurality of first follicular maps.

Clause 13B. The analysis unit according to clause 13A, the zero-loss processor being arranged to output the combined first follicular map to the image processor for use as the first or second follicular map.

Clause 13C. The analysis unit according to clause 13A or 13B, the zero-loss processor being arranged to output the combined input image to the image processor for use as the first or second videodermoscopy image.

Clause 14. A system for assessment of hair condition, the system comprising:
an upload unit,
an analysis unit according to any one of the preceding clauses, and
a presentation unit,
the upload unit being arranged to receive one or more videodermoscopy images, the one or more videodermoscopy images comprising at least the first videodermoscopy image and to upload the one or more videodermoscopy images to the analysis unit, the analysis unit being arranged to receive the one or more videodermoscopy images from the upload unit and to obtain a videodermoscopic analysis result from the one or more videodermoscopy images, the videodermoscopic analysis result comprising at least one of:
  the analysis result suitable for assessment of hair condition, and
  an examination result derived from at least one of the analysis result suitable for assessment of hair condition, and
the presentation unit being arranged to receive the videodermoscopic analysis result from the analysis unit and to present at least part of the analysis result to a user.

Clause 15. The system according to clause 14, the system further comprising a result check unit, the result check unit being arranged to:
  receive the videodermoscopic analysis result from the analysis unit,
  review the videodermoscopic analysis result and to modify the videodermoscopic analysis result, and
  provide the videodermoscopic analysis result as modified to the presentation unit to allow the presentation unit to present at least part of the videodermoscopic analysis result as modified to the user.

Clause 16. The system according to any one of clauses 14-15, the upload unit and//or the presentation unit being connected to the analysis unit via a communication network.

Clause 17. A method for assessment of hair condition, the method comprising:
  obtaining a first follicular map representing a first plurality of hair root positions in a first videodermoscopy image, and
  analysing at least the first follicular map to determine an analysis result suitable for assessment of hair condition.

Clause 18. The method of clause 17, the method further comprising performing an image processing algorithm on a first videodermoscopy image to obtain the first follicular map representing the first plurality of hair root positions in the first videodermoscopy image.

Clause 19. The method of clause 17 or 18, the method further comprising:
  obtaining a second follicular map representing a second plurality of hair root positions in a second videodermoscopy image, and
  determining a common skin area from the first follicular map and the second follicular map.

Clause 19A. A method for assessment of hair condition, the method comprising:
  obtaining a first follicular map representing a first plurality of hair root positions in a first videodermoscopy image,
  obtaining a second follicular map representing a second plurality of hair root positions in a second videodermoscopy image,
  determining a common skin area from the first follicular map and the second follicular map,
  relating hair root positions in the second follicular map to hair root positions of the first follicular map in the common skin area to determine a plurality of related hair root positions, each related hair root position of a hair root in the second follicular map being related to a hair root position in the first follicular map of the same hair root; and
  comparing a change in condition of individual hair between the first and second videodermoscopy image to determine the analysis result suitable for assessment of hair condition.

Clause 20. The method of clause 19 or 19A, the method further comprising performing an image processing algorithm on a second videodermoscopy image to obtain the second follicular map representing the second plurality of hair root positions in the second videodermoscopy image.

Clause 21. A computer program product comprising a computer program comprising instructions arranged to, when executed by a computer, execute at least part of the method of any one of clauses 17-20.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same or corresponding structural features and the same or corresponding functions, or are the same or corresponding signals. Where the function and/or structure of such an item has been explained, there is no necessity for repeated explanation thereof in the detailed description.

DETAILED DESCRIPTION

Figure 1:
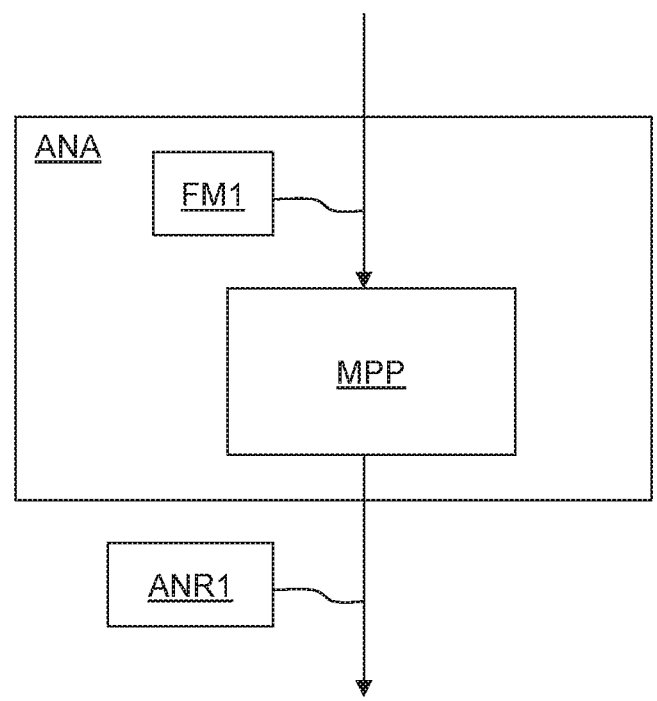
FIG. 1 shows an analysis unit for assessment of hair condition according to an embodiment.

FIG. 1 shows an analysis unit ANA for assessment of hair condition according to an embodiment. The analysis unit ANA comprises a map processor MPP. The map processor is arranged to at least obtain a first follicular map FM1 representing a first plurality of hair root positions in a first videodermoscopy image. The map processor is further arranged to analyse at least the first follicular map FM1 to determine an analysis result ANR1 suitable for assessment of hair condition.

The map processor MPP may be arranged to obtain the first follicular map FM1 from a storage. The map processor MPP may be arranged to obtain the first follicular map FM1 from receiving the first follicular map FM1 over a communication channel, such as from a communication network. The map processor may obtain the first follicular map from a storage, such as from a patient database wherein the first follicular map is stored. The map processor may alternatively obtain the first follicular map from an image processor that is arranged to generate the first follicular map from a first videodermoscopy image.

Examination of hair condition may relate to diagnosis of hair disorders. Examination of hair condition may additionally or alternatively relate to identification and/or measurement of an advancement of hair disorder, measurement of a result of a treatment of a hair disorder, measurement of an effect and/or effectiveness of a medical treatment, or measurement of an effect and/or effectiveness of a cosmetic treatment.

The analysis result may, e.g., comprise an average hair root density, an average distance between hair roots, statistical parameters representing a statistics of distances between hair roots, or another parameter derivable from hair root positions.

Figure 2:
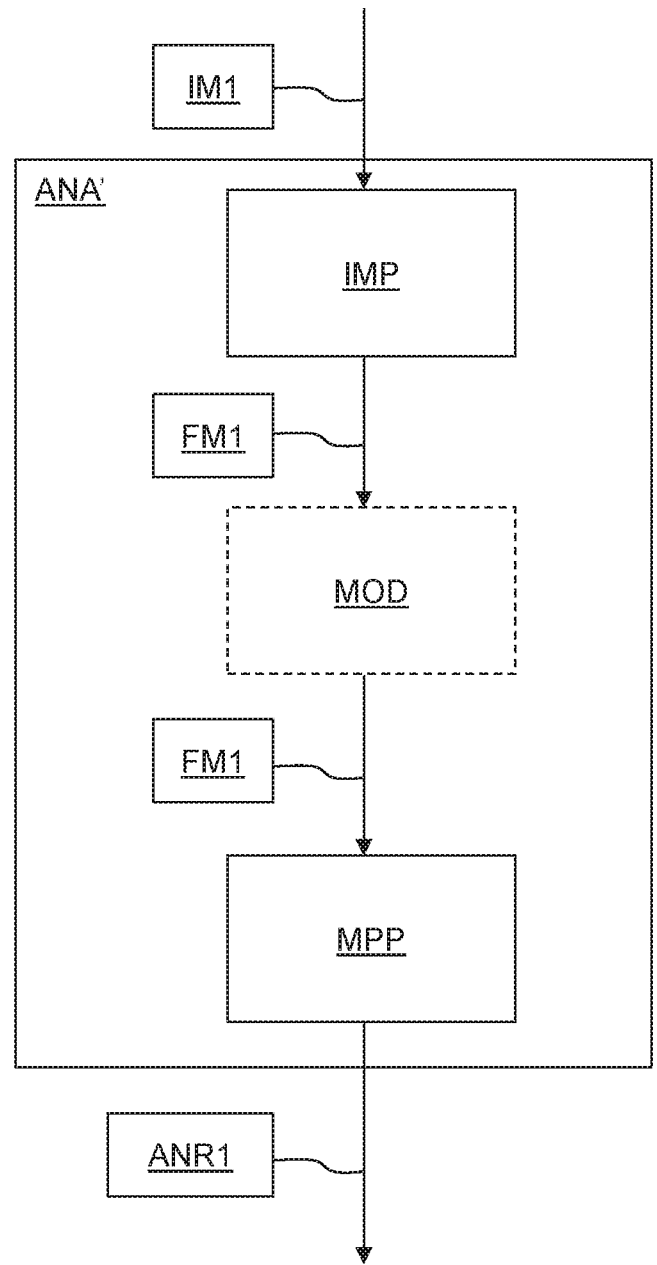
FIG. 2 shows an analysis unit for assessment of hair condition according to a further embodiment, FIG. 3a and FIG. 3b schematically shows distributions measured in follicular maps of a first and a second person respectively.

FIG. 2 shows a further embodiment of an analysis unit ANA' for assessment of hair condition according to an embodiment. The analysis unit ANA' comprises an image processor IMP and a map processor MPP. The image processor IMP is arranged to perform an image processing algorithm on a first videodermoscopy image IM1 to generate a first follicular map FM1 representing a first plurality of hair root positions in the first videodermoscopy image IM1. The map processor MPP is arranged to obtain the first follicular map from the image processor IMP. As in the embodiment shown in FIG. 1, the map processor is further arranged to analyse at least the first follicular map FM1 to determine an analysis result ANR1 suitable for assessment of hair condition.

The map processor may be connected to the image processor and arranged to obtain the first follicular map directly from the image processor. The map processor may be connected to the image processor via one or more intermediate devices or channels and the map processor is arranged to obtain the first follicular map from the image processor via the one or more intermediate devices or channels. In an embodiment, the map processor is connected to a storage unit, the image processor is connected to the storage unit, the image processor is arranged to store the first follicular map in the storage unit, and the map processor is arranged to obtain the first follicular map from the image processor by retrieving it from the storage unit. The retrieval from the storage unit may occur substantially immediately after the first follicular map was stored in the storage unit by the image processor. The retrieval from the storage unit may alternatively occur at a much later moment in time than when the first follicular map was stored in the storage unit by the image processor, to allow a later analysis of the first follicular map, for example, when a second follicular map has become available after a period of time, to allow to compare a change of the follicular map over time to support the examination of symptoms of hair diseases.

The image processing algorithm performed on the first videodermoscopy image IM1 to generate the first follicular map FM1 representing the first plurality of hair root positions in the first videodermoscopy image IM1, may comprise any combination of suitable pattern recognition algorithms and qualification algorithms, such as binarization, adaptive thresholding, noise detection, blob detection, blob recombination, line tracking, hair crossing recombination, end detection, watershed division, and tip-follicle qualification.—The image processing algorithm may be supplemented by a manual correction by operators, for, e.g., removal of mistakes, addition of non-detected hair, removal of falsely detected hair, addition or removal of hair follicles. The spatial coordinates of the hair follicles identified in the field of view of the first videodermoscopy image may be referred to as the first follicular map FM1. The first follicular map FM1 thus represents the first plurality of hair root positions in the first videodermoscopy image IM1. The first follicular map FM1 may be stored and/or presented as a list of spatial coordinates, such as (x, y) coordinates in the first videodermoscopy image IM1, as a graphical representation, or in any other suitable form. The first follicular map FM1 may, e.g., be presented on screen together with the first videodermoscopy image, such as side-by-side with the first videodermoscopy image or as an overlay on the first videodermoscopy image.

FIG. 2 thus shows an embodiment of an analysis unit ANA' for assessment of hair condition, the analysis unit comprising an image processor IMP arranged to at least perform an image processing algorithm on a first videodermoscopy image IM1 to obtain a first follicular map FM1 representing a first plurality of hair root positions in the first videodermoscopy image IM1, and a map processor MPP arranged to analyse at least the first follicular map FM1 to determine an analysis result ANR1 suitable for assessment of hair condition.

FIG. 2 further that, in further embodiments, the analysis unit ANA' may comprise a map modification unit MOD. The image processor IMP is arranged to, as part of obtaining the first follicular map FM1, cooperate with the map modification unit MOD. The map modification unit MOD is arranged to present the first follicular map FM1 as obtained from the performing of the image processing algorithm on the first videodermoscopy image to a human assistant, and allow the human assistant to review the first follicular map FM1 and to modify the first follicular map FM1 such as to, at least, add and/or remove one or more hair root positions from the first follicular map FM1. The first follicular map as reviewed and modified is thereafter used for analyzing at least the first follicular map to determine the analysis result suitable for assessment of hair condition. Using review by human assistants may improve the quality of the follicular map significantly. In further embodiments, the map modification unit MOD is further arranged to present the first follicular map FM1 as obtained from the performing of the image processing algorithm on the first videodermoscopy image IM1 to a plurality of human assistants, to allow each of the human assistant to review the first follicular map and to propose to modify the first follicular map such as to, at least, add and/or remove one or more hair root positions from the first follicular map. In these embodiments, the map modification unit MOD may be arranged to compare the proposals from the plurality of human assistants for removing one or more hair root positions from the first follicular map FM1, and to decide from the comparison which hair root position of the proposed one or more hair root positions from the first follicular map to delete. For example, the map modification unit MOD may be arranged to use a majority voting in deciding which of the proposed one or more hair root positions is to be deleted. Using majority voting of a plurality of reviews by human assistants may improve the quality of the follicular map even further.

In the embodiments shown in FIG. 1 and FIG. 2, as well as in further embodiments, the map processor MPP may be arranged to, as part of analysing at least the first follicular map to determine the analysis result, perform a statistical analysis of hair root distances between hair roots positions of the first plurality of hair root positions.

Herein, the map processor MPP may be arranged to, as part of performing the statistical analysis of hair root distances between hair root positions, determine a hair root distance distribution, and determine at least a first and a second relative contribution to the hair root distance distribution of at least a first and a second distribution component function.

For example, the first and second relative contributions may be obtained from, a two-component fit to the distribution, with the first contribution reflecting the dominant component for a specific hair disorder and the second contribution reflecting the dominant component for healthy hair. Optionally more contributions may be used reflecting respective dominant component for other specific hair disorders.

Figure 3A:
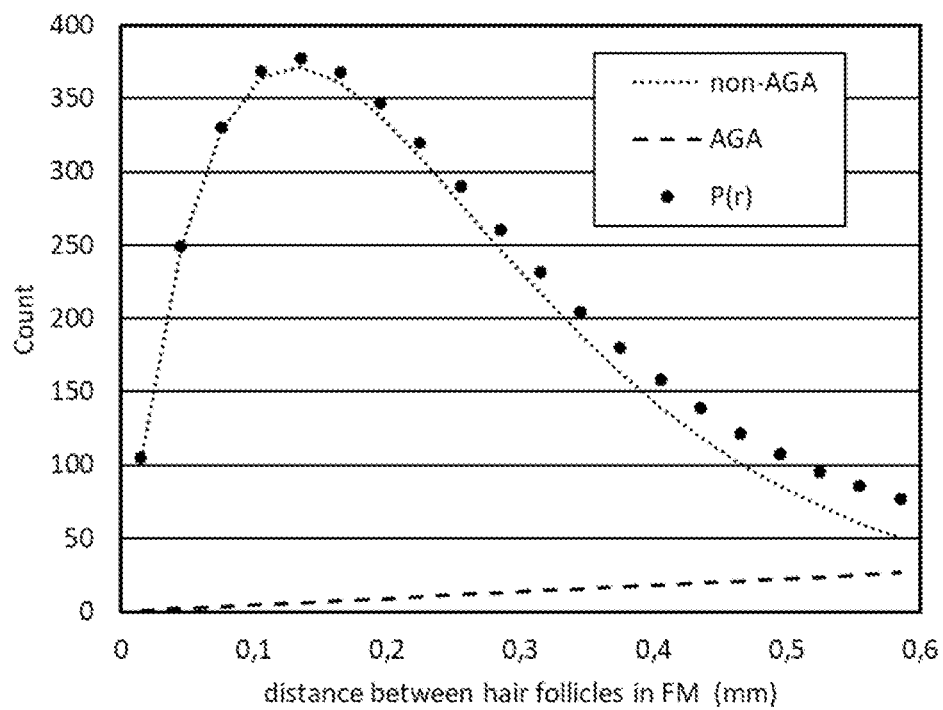
Figure 3B:
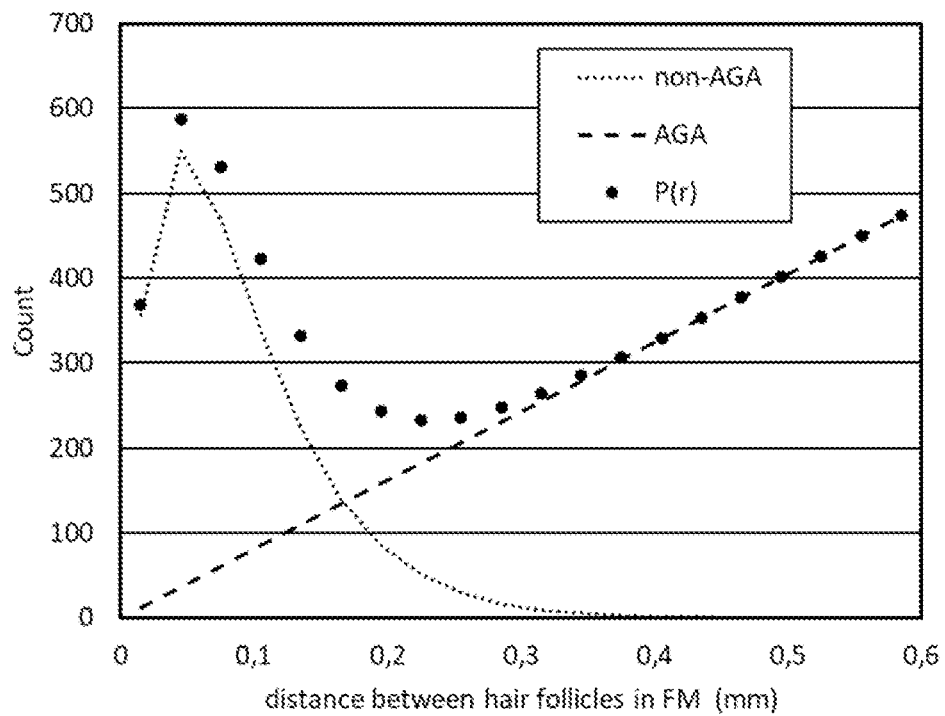

In an embodiment, the relative contribution of the first distribution component function being an indication for a degree of a hair disorder of a first type. E.g., when the relative contribution is found to be in a first indicator range, such as larger than 35%, this may be an indication of androgenetic alopecia (AGA). An example is shown in FIG. 3a and FIG. 3b. FIG. 3a shows the distribution of distances to all other hair follicles in the follicular map of a first, healthy, person. FIG. 3b shows the distribution of distances to all other hair follicles in the follicular map of a second person who has AGA in an advanced stage. In each Figure, the resulting distribution, indicated as points P(r), is fitted in the low distance range (in this example, distances r<600 μm) by a model consisting of a sum of two components: a first component labeled AGA that is a linear distribution, and a second component labeled non-AGA that is peaked at low values and has a varying width. The first component represents a distribution that is characteristic for AGA. The second component represents a distribution that is characteristic for healthy individuals. The relative contribution of the first component provides a measure to assess AGA advancement.

Figure 4:
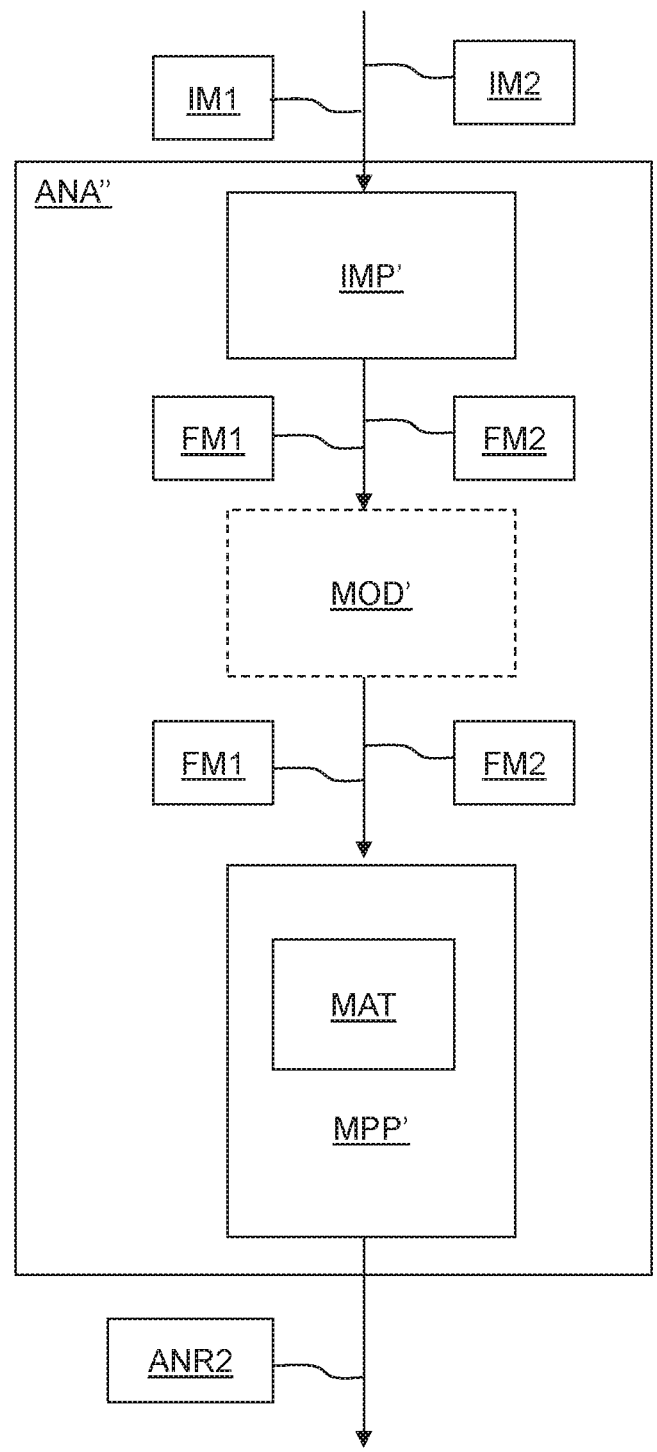
FIG. 4 shows an analysis unit for assessment of hair condition according to another embodiment, FIG. 5 schematically shows a first and second follicular map and the common skin area, FIG. 6 schematically shows an analysis unit according to another embodiment, FIG. 7 schematically shows a use of a videodermoscopy camera according to an embodiment, FIG. 8 schematically shows videodermoscopy images and follicular maps to illustrate the embodiment of FIG. 6, FIG. 9 schematically shows an analysis unit for assessment of hair condition according to again another embodiment, FIG. 10 schematically shows an analysis unit for assessment of hair condition according to again another embodiment, FIG. 11 schematically shows a zero-loss processor according to an embodiment, FIG. 12 schematically shows videodermoscopy images and follicular maps to illustrate the zero-loss processor of FIG. 11, FIG. 13 schematically shows a system SYS for assessment of hair condition, FIG. 14-FIG. 16 schematically show methods for assessment of hair condition according to embodiments, FIG. 17 schematically shows a method of zero-loss videodermoscopic image processing according to an embodiment.

FIG. 4 shows an analysis unit ANA" for assessment of hair condition according to another embodiment. The analysis unit ANA" comprises a map processor MPP'. The map processor MPP' is arranged to at least obtain a first follicular map FM1 representing a first plurality of hair root positions in a first videodermoscopy image and a second follicular map FM2 representing a second plurality of hair root positions in a second videodermoscopy image. The map processor MPP' is further arranged to analyse at least the first follicular map FM1 and the second follicular map FM2 to determine an analysis result ANR2 suitable for assessment of hair condition.

The map processor MPP' may, similarly as described with respect to the map processors shown in FIG. 1 and FIG. 2, obtain the first and second follicular map FM1, FM2 from retrieving the maps from a storage, receiving them from a communication network, or receive them from the image processor IMP'. For example, the image processor IMP' may be further arranged to perform an image processing algorithm on a second videodermoscopy image to generate the second follicular map representing the second plurality of hair root positions in the second videodermoscopy image, and the map processor MPP' may be arranged to obtain the second follicular map from the image processor.

Similar to analysis unit ANA' shown in FIG. 2, the analysis unit ANA" may comprise a map modification unit MOD'. The image processor IMP is arranged to, as part of obtaining the first follicular map FM1 as well as part of obtaining the second follicular map FM2, cooperate with the map modification unit MOD'. The map modification unit MOD' is arranged to present the first and second follicular maps FM1, FM2 as obtained from the performing of the image processing algorithm on the first and second videodermoscopy image to a human assistant, and allow the human assistant to review the first and second follicular map FM1, FM2 and to modify the first and second follicular map FM1, FM2 such as to, at least, add and/or remove one or more hair root positions from the first and/or second follicular map FM1, FM2. The first and second follicular map as reviewed and modified is thereafter used for analyzing at least the first and second follicular map to determine the analysis result suitable for assessment of hair condition.

Figure 5:
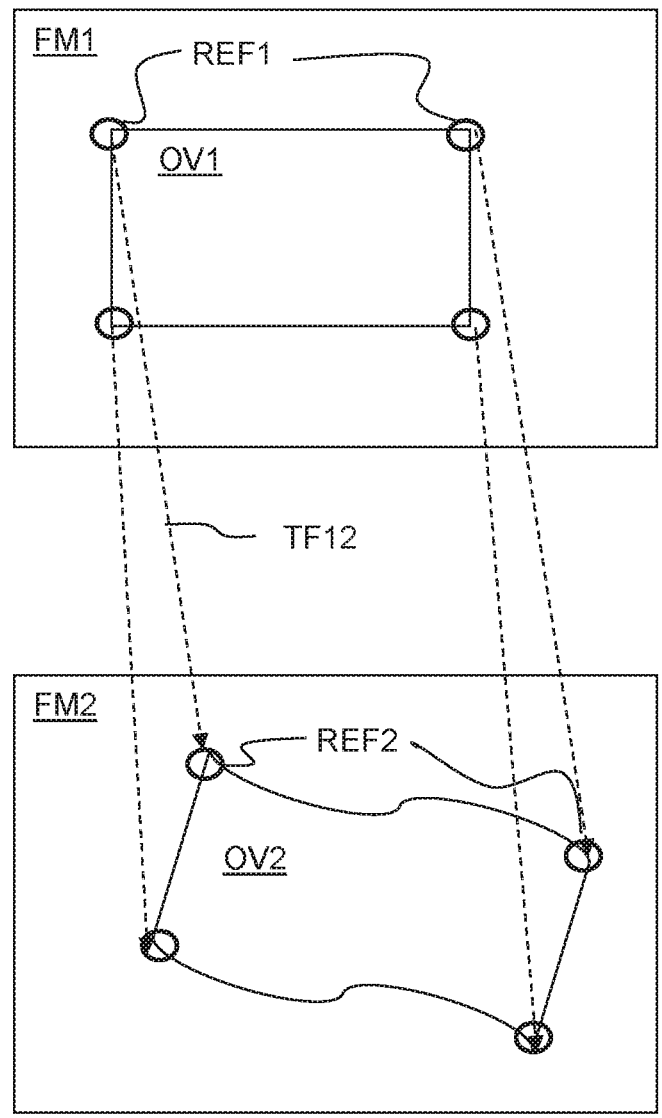

In an embodiment, the map processor MPP' is further arranged to determine a common skin area from the first follicular map FM1 and the second follicular map FM2. This is illustrated in FIG. 5. FIG. 5 schematically shows a first and second follicular map FM1, FM2 and the common skin area. The common skin area thus corresponds to a part OV1 of the first follicular map FM1 that corresponds to a part OV2 of the second follicular map FM2 which corresponds to the same skin area as the part OV1 of the first follicular map FM1. These parts may further be referred to as the common skin area OV1 of the first follicular map FM1 and the common skin area OV2 of the second follicular map FM2. The map processor MPP' may be arranged to as part of determining the common skin area from the first follicular map FM1 and the second follicular map FM2, determine a transformation function TF12 which relates hair root positions in the first follicular map FM1 to hair root positions of the same hair in the second follicular map FM2. The common skin area OV1 of the first follicular map FM1 may thus be related to the common skin area OV2 of the second follicular map FM2 by transformation function TF12 as schematically illustrated in FIG. 5. When the first follicular map FM1 relates to a first videodermoscopy image registered at a first moment in time, such as before a treatment, and the second follicular map FM2 relates to a second videodermoscopy image registered at a second later moment in time, such as after the treatment, analyzing differences between the common skin area of the first follicular map FM1 and the common skin area of the second follicular map FM2 and/or analyzing differences between the common skin area of the first videodermoscopy image IM1 and the common skin area of the second videodermoscopy image IM2 may allow a largely improved precision compared to known techniques. Using the follicular maps to identify the common skin area, i.e., corresponding skin areas in both follicular maps, largely improves the precision of the analysis. Whereas prior art techniques relied strongly on exactly the same positioning of the camera on the skin and the same field of view, the use of the matching follicular maps makes the analysis largely independent of size, shape and distortion of the area used for the videodermoscopic analysis. The size, shape and distortion of the area of the skin registered on a videodermoscopy image may vary significantly when two images are registered at different moments in time and/or different locations. For example, if the skin is stretched or displaced by pressing the videodermoscopic lens, the actual measurement area may differ up to 30%, which results in an inaccurate analysis with known techniques.

For example, identifying which of the hair root positions in the first follicular map FM1, and hence which hair in the first videodermoscopy image IM1 corresponds to which of the hair root positions in the second follicular map FM2, and hence which hair in the second videodermoscopy image IM2, allows an accurate determination of which hair has appeared and which hair has disappeared, based on tracking individual hair rather than mere statistics over the overlap area. E.g., instead of determining that the number of hair has increased from 100 to 105 for a specific subject after a certain period of time, it may be determined that 5 hair were lost and 10 came new. Such knowledge may be of relevance when assessing certain kinds of hair disorder. For determination of therapeutic effects of new substances in clinical trials, this technique and the corresponding precision improvement, may allow to reduce the number of test patient samples necessary to obtained conclusive result.

As shown in FIG. 4, the map processor MPP' may a matching unit MAT. The matching unit MAT may be arranged to at least relate hair root positions in the second follicular map to hair root positions of the first follicular map in at least the common skin area to determine a plurality of related hair root positions. Each related hair root position of a hair root in the second follicular map may thus be related to a hair root position in the first follicular map of the same hair root. This may be performed as part of determining the common skin area, or after the common skin are has been determined. Hereby, the method determines relates hair root positions of the second plurality of hair root positions in the second videodermoscopy image to hair root positions of the first plurality of hair root positions in the first videodermoscopy image in at least the common skin area to determine related hair root positions.

The map processor MPP' may be arranged to, in determining the common skin area from at least analyzing the first plurality of positions of hair roots and the second plurality of positions of hair roots, find corresponding positions of hair roots by minimizing their relative distance in one or more iterations.

In embodiments, the matching unit MAP is arranged to, as part of relating hair root positions and/or while determining a common skin area from the first follicular map FM1 and the second follicular map FM2, initialize a transformation function TF12 and iteratively adapt the transformation function TF12. The iterative adaption comprises:
  applying the transformation function TF12 to the first plurality of hair root positions of the first follicular map FM1 to obtain a first plurality of transformed hair root positions,
  relating the first plurality of transformed hair root positions to the second plurality of hair root positions of the second follicular map FM2,
  determining relative distances between transformed hair root positions of the first plurality of transformed hair root positions and the related hair root positions of the second plurality of hair root positions to obtain a correspondence metric, and
  adapting the transformation function TF12 to minimize the correspondence metric.

In further embodiments, the matching unit MAP is arranged to, as part of iteratively adapting the transformation function, further use at least one parameter of hair associated with the transformed hair root positions and hair associated with the related hair root positions to obtain the correspondence metric, the at least one parameter comprising at least one parameter from a group consisting of hair shaft diameter, hair length, hair growth, hair color.

In further embodiments, the matching unit MAP is arranged to, as part of initializing the transformation function TF, detect positions of a first plurality of reference symbols REF1 on the skin in the first videodermoscopy image IM1, detect positions of a second plurality of reference symbols REF2 on the skin in the second videodermoscopy image IM2, initialize the transformation function TF12 to reflect a transformation from the positions of a first plurality of reference symbols REF1 to the positions of a second plurality of reference symbols REF2.

The first and second plurality of reference symbols REF1, REF2 may be a plurality of micro-tattoos on the skin, for example 2, 3, 4, 6, 9, 16 or any suitable number of micro-tattoos. The micro-tattoos may, as in known methods, be used to roughly position the videodermoscope at roughly corresponding positions on the skin to register suitable videodermoscopy images at subsequent moments in time.

The map processor MPP' may be further arranged to at least analyse differences between at least the common skin area OV1 in the first follicular map FM1 and the common skin area OV2 in the second follicular map FM2 to determine the analysis result suitable for assessment of hair condition. The map processor MPP' may thus analyze differences between hair root positions, number of hair roots and hair root density. The first follicular map fm1 may, e.g., be associated with a first videodermoscopy image im1 registered before the start of a treatment, and the second follicular map FM2 may associated with a second videodermoscopy image IM2 registered after a certain duration of the treatment. Analysing the differences may then give an analysis result suitable for supporting the examination of hair condition, in particular whether symptoms have changed as a result of the treatment. The map processor MPP' may be arranged to, in determining the analysis result, identify an appearing of new hair roots in the common skin area in the second follicular map compared to the common skin area in the first follicular map. The map processor MPP' may provide the appearing of new hair roots as an indication of new growth as part of the analysis result. The map processor MPP' may be arranged to, in determining the analysis result, identify a disappearing of hair roots from the common skin area in the second follicular map compared to the common skin area in the first follicular map. The map processor MPP' may provide the disappearing of hair roots as an indication of hair loss as part of the analysis result. The map processor MPP' may be arranged to, in determining the analysis result, determine a difference in total number of hair roots in the common skin area OV2 in the second follicular map FM1 compared to the common skin area OV1 in the first follicular map OV2. The map processor MPP' may be arranged to, in determining the analysis result, determine a difference in hair density in the common skin area OV2 in the second follicular map FM2 compared to the common skin area OV1 in the first follicular map FM1.

In further or alternative embodiments, the map processor MPP' is arranged to at least analyse differences between at least the common skin area in the first videodermoscopy image IM1 and the common skin area in the second videodermoscopy image IM2 to determine the analysis result suitable for assessment of hair condition. The map processor MPP' may thus analyze differences between hair in the common skin area of the first videodermoscopy image IM1 and hair in the common skin area in the second videodermoscopy image IM2. Individual hair may be compared as for each hair in the first videodermoscopy image IM1, the related hair in the second videodermoscopy image IM2 can be identified, e.g. by applying the transformation function TF12 to the hair root position from the first follicular map FM1 to find the related hair root position in the second follicular map FM2. The first videodermoscopy image IM1 may have been registered before the start of a treatment, and the second videodermoscopy IM2 image may have been registered after a certain duration of the treatment. Analysing the differences may then give an analysis result suitable for supporting the examination of hair condition, in particular whether symptoms have changed as a result of the treatment. The map processor MPP' may hereto be arranged to, in analyse differences between at least the common skin area in the first videodermoscopy image and the common skin area in the second videodermoscopy image, determine differences between at least one parameters of a group of parameters consisting of average hair diameter, hair diameter distribution, average hair length, hair length distribution, hair colors, hair color distribution, and/or at least one hair density.

According to an exemplary embodiment, the first videodermoscopy image IM1 was captured before shaving and the second videodermoscopy image IM2 was captured after shaving, and the map processor MPP' is arranged to compare lengths of individual hairs between the common skin area in the first videodermoscopy image IM1 and lengths of the same individual hairs in the common skin area in the second videodermoscopy image IM2. Comparing the change in lengths may be performed by determining a length decrease, such as to provide an indication of the hair length decrease and thereby an indication of the shaving performance.

According to another exemplary embodiment, the first videodermoscopy image IM1 was captured immediately or shortly after shaving and the second videodermoscopy image IM2 was captured significantly later after shaving, such as after 3-5 days, and the map processor MPP' is arranged to compare lengths of individual hairs between common skin area in the first videodermoscopy image IM1 and lengths of the same individual hairs in the common skin area in the second videodermoscopy image IM2, to determine changes of length—in particular length increases by hair growth—for the individual hairs, and to calculate estimates of the lengths of individual hairs immediately after shaving from the changes of lengths. Hereby, an indication of the quality of close shaving may be provided. In case a razor blade arranged to pull hair out and cut the hair effectively below skin surface was used, the estimates may provide negative lengths of individual hair as a result of the shaving. The analysis result suitable for assessment of hair condition may thus be a set of negative lengths of individual hair, reflecting the hair condition after shaving, or one or more statistical parameters measured on the set of negative lengths of individual hair reflecting statistical performance indicators of the hair condition after shaving.

The first videodermoscopy image IM1 may e.g. be captured a few minutes, a few hours, or 1 or 2 days after shaving. When capturing after 1 or 2 days, the hair has generally grown enough for a reliable detection of hair root positions. The second videodermoscopy image IM2 may e.g. be captured 3-5 days after shaving, which give enough time between the capturing of the images for the hair to grow such that a growth rate can be estimated for a reliable and sufficiently accurate estimates of the lengths immediately after shaving. For example, the first videodermoscopy image IM1 may e.g. be captured 1 day after shaving and the second videodermoscopy image IM2 may e.g. be captured 3 days after shaving. As another example, the first videodermoscopy image IM1 may e.g. be captured 2 days after shaving and the second videodermoscopy image IM2 may e.g. be captured 5 days after shaving.

According to another exemplary embodiment, the first videodermoscopy image IM1 was captured before epilation and the second videodermoscopy image IM2 was captured after epilation. The map processor MPP' may be arranged to, e.g., compare presence and/or diameters and/or lengths of individual hair between the first videodermoscopy image captured from a part of a skin before epilation and presence and/or diameters and/or lengths of the same individual hair in a second videodermoscopy image captured from the same part after epilation as part of an examination of epilation performance on hair condition, in particular hair extraction, hair diameter and hair length. Hereby, an analysis result suitable for the assessment of hair condition may be obtained which is indicative for the epilation performance. This embodiment provides estimates of the positions of individual hair follicles and the correspondence between hair follicle locations between the first and second follicular maps, which allows, e.g., to determine which hair was successfully extracted, to compare individual hair before and after epilation, to evaluate the remaining hair and, in particular when also incorporating regrowth parameters, to distinguish between empty and damaged hair follicles.

According to another exemplary embodiment, the first videodermoscopy image IM1 was captured immediately or shortly after epilation and the second videodermoscopy image IM2 was captured significantly later after epilation, such as after 3-5 days. The map processor MPP' may be arranged to, e.g., analyze regrowth for diameter and length increase to determine a degree of hair follicle damage as part of the analysis result.

Figure 6:
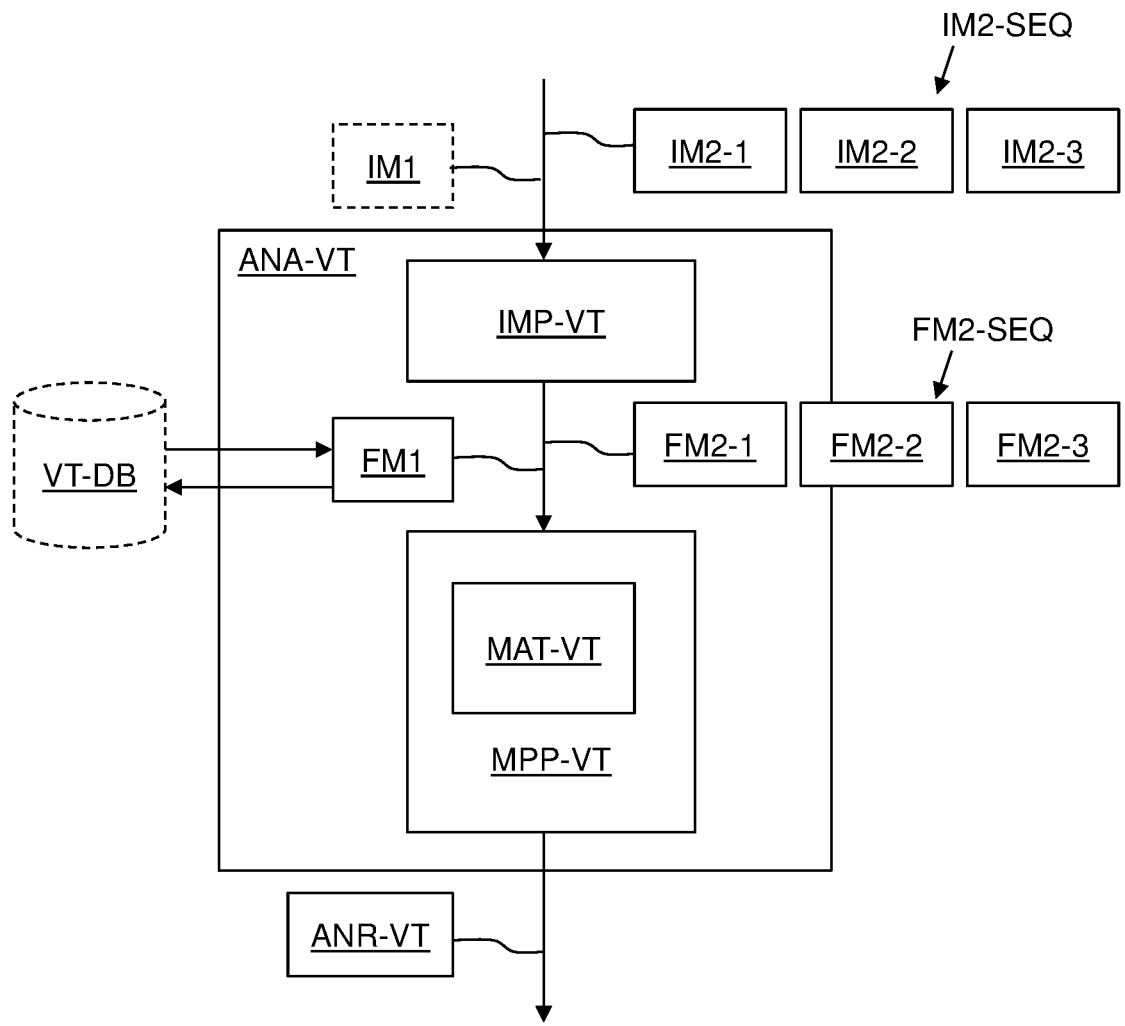

FIG. 6 shows an analysis unit ANA-VT according to another embodiment. The analysis unit ANA-VT comprises a map processor MPP-VT. The map processor MPP-VT is arranged to at least obtain a first follicular map FM1 representing a first plurality of hair root positions in a first videodermoscopy image and a sequence FM2-SEQ of second follicular maps FM2-1, FM2-2, FM2-3, each representing a plurality of hair root positions in associated second videodermoscopy images IM2-1, IM2-2, IM2-3 of a sequence IM2-SEQ of different second videodermoscopy images. The second videodermoscopy images IM2-1, IM2-2, IM2-3 of the sequence IM2-SEQ may correspond to videodermoscopy images acquired from different locations on the skin, for example as images from adjacent parts or overlapping parts of the skin. The second videodermoscopy images IM2-1, IM2-2, IM2-3 of the sequence IM2-SEQ may correspond to videodermoscopy images acquired from changing the position of the videodesmoscope between registering successive second videodermoscopy images, e.g., while moving the videodesmocope along a part of a skin in a scanning direction. The map processor MPP-VT is further arranged to analyse at least the first follicular map FM1 and the sequence of second follicular maps FM2-1, FM2-2, FM2-3 to determine an analysis result ANR2-VT suitable for assessment of hair condition. The map processor MPP-VT may alternatively or additionally be arranged to determine an analysis result suitable for assessment of skin condition, such as detecting, measuring or monitoring skin color, skin color variation, presence and growth of birthmarks, naevus, scars, and their development over time.

Figure 7:
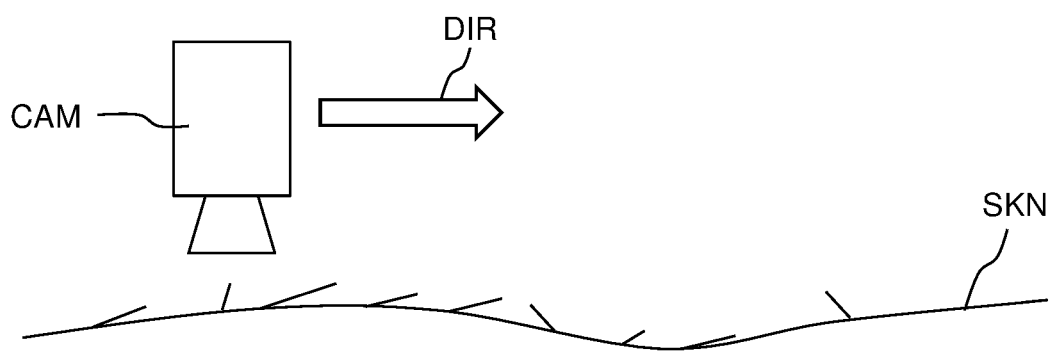

The analysis unit ANA-VT shown in FIG. 6 comprises an image processor IMP-VT arranged to perform an image processing algorithm on each second videodermoscopy image of the sequence of second videodermoscopy image IM2-1, IM2-2, IM2-3 to generate the sequence of second follicular maps FM2-1, FM2-2, FM2-3, each second follicular map representing an associated second plurality of hair root positions in the associated second videodermoscopy image IM2-1, IM2-2, IM2-3. As illustrated in FIG. 7, a videodermoscopy camera CAM or another suitable camera may be used to obtain the sequence of second videodermoscopy image IM2-1, IM2-2, IM2-3 while moving the camera CAM along a part of a skin SKN in a scanning direction DIR. Moving the camera may be performed as a continuous movement along the scanning direction and registering each of the of second videodermoscopy images of the sequence of second videodermoscopy images may be performed while the camera is moving. Moving the camera CAM may alternatively be performed in a step-wise manner, where the moving comprises repositioning the camera between successive imaging locations of a sequence of different successive imaging locations along the scanning direction for registering each of the second videodermoscopy images of the sequence of second videodermoscopy images at a respective one of the successive imaging locations. The camera CAM may obtain the sequence of second videodermoscopy images such that successive second videodermoscopy images of the sequence of second videodermoscopy images are partly overlapping. Hereby, the sequence of second videodermoscopy images effective registeres a large strip of the skin. The camera CAM may obtain the sequence of second videodermoscopy images as a sequence of still images taken, for example, at a fixed or varying time interval in a range of 10 ms to 5 seconds, or at any other suitable time interval. The camera CAM may alternatively obtain the sequence of second videodermoscopy images as a video sequence having a frame rate in, for example, a range of 10-100 Hz, e.g. at a frame rate of 16.7, 25, 50, 60 or 100 Hz, or at any other suitable frame rate. The sequence may be provided offline to the image processor IMP-VT. The sequence may be provided real-time to the image processor IMP-VT, and the image processor IMP-VT may be arranged to generate the sequence of second follicular maps FM2-1, FM2-2, FM2-3 real-time from the sequence of second videodermoscopy images IM2-1, IM2-2, IM2-3.

The image processor IMP-VT may further be arranged to perform an image processing algorithm on the first videodermoscopy IM1 to generate the first follicular maps FM1, but the first follicular maps FM1 may have been determined at an earlier moment in time and stored in a database VT-DB for retrieval when the analysis unit operates on a second videodermoscopy images of the same person for, e.g., obtaining an analysis suitable for assessing a change in hair condition.

The map processor MPP-VT is further arranged to determine a common skin area from the first follicular map FM1 and the sequence of second follicular maps FM2-1, FM2-3, FM2-3. Herein, the map processor MPP-VT may be arranged to determine which second follicular map of the sequence FM2-1, FM2-3, FM2-3 matches the first follicular map FM1 best, as illustrated in FIG. 8.

Hereto, the analysis unit ANA-VT may comprises a matching unit MAT-VT, similar to the embodiment described with reference to FIG. 4. The matching unit MAT-VT may be arranged to at least relate hair root positions in each of the second follicular maps FM2-1, FM2-2, FM2-3 to hair root positions of the first follicular map FM1 in at least the common skin area to determine a plurality of related hair root positions. For each of the second follicular maps FM2-1, FM2-2, FM2-3, the matching unit MAT-VT aims to relate each related hair root position of a hair root in respective the second follicular map to a hair root position in the first follicular map FM1 of the same hair root. This may be performed as part of determining the common skin area, or after the common skin are has been determined. Hereby, the method relates, for each of the second follicular maps FM2-1, FM2-2, FM2-3, hair root positions of the respective second plurality of hair root positions in the respective second videodermoscopy image to hair root positions of the first plurality of hair root positions in the first videodermoscopy image in at least the common skin area to determine related hair root positions. The map processor MPP-VT is arranged to, in determining the common skin area from at least analyzing the first plurality of positions of hair roots in the first follicular map FM1 and the second plurality of positions of hair roots in each of the second follicular maps FM2-1, FM2-2, FM2-3, find corresponding positions of hair roots by minimizing their relative distance in one or more iterations. Reference is further made to the description of the matching unit MAT of FIG. 4.

Figure 8:
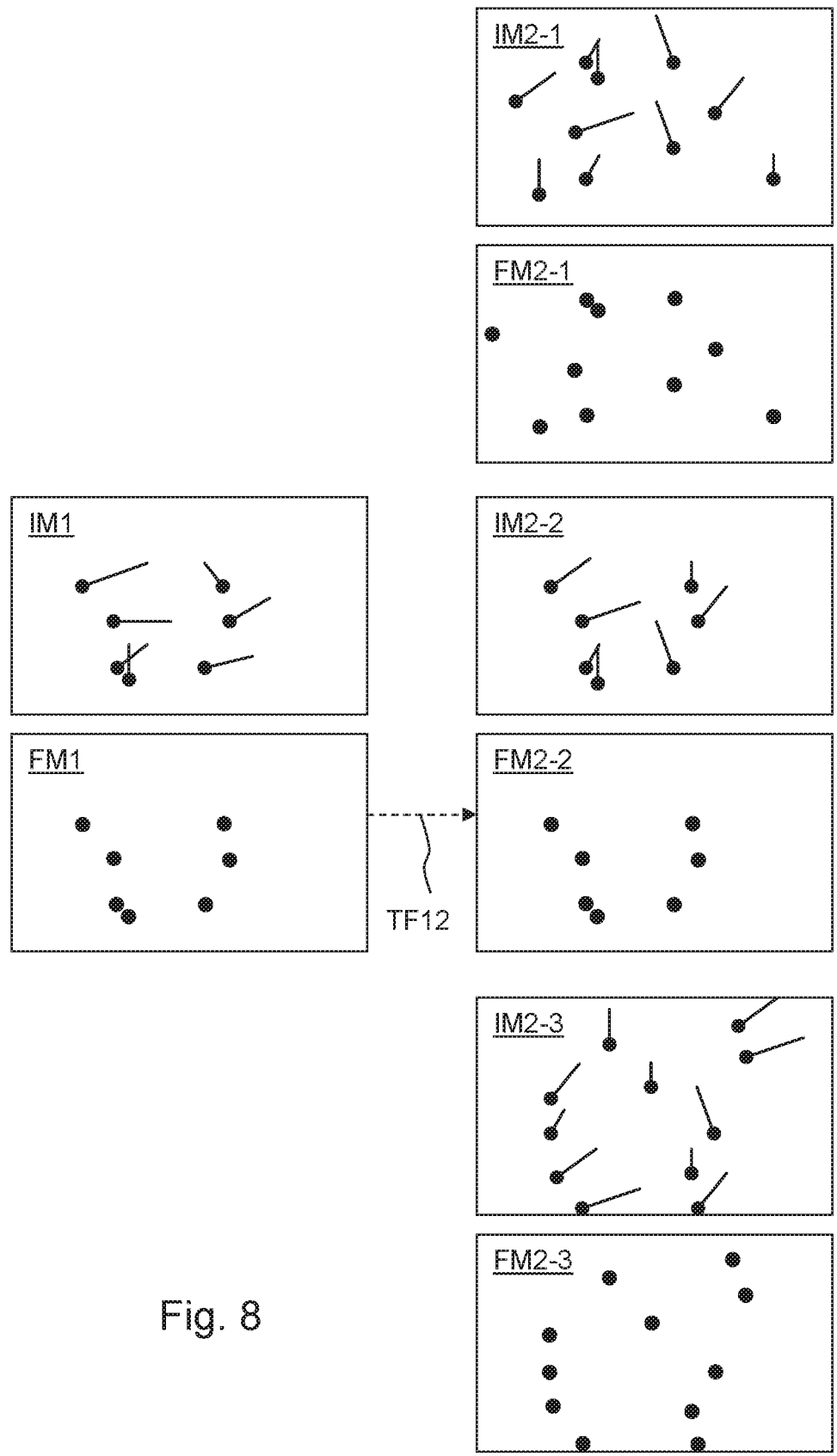

FIG. 8 schematically shows, on the left, a first videodermoscopy image IM1 and its first follicular map FM1. The right column shows a sequence of second videodermoscopy images IM2-1, IM2-2, IM2-3 and the associated sequence of second follicular maps FM2-1, FM2-2, FM2-3. The camera position was moved by half of the image height between IM2-1 and IM2-2, and again between IM2-2 and IM2-3, thereby generating overlapping images. However, the images may also be adjacent or have a gap in between, as long as the size of the overlapping area between the first follicular map FM1 and best matching second follicular map of the sequence is adequate for determining an analysis result. It may be seen from the Figure that the second follicular map FM2-2 of the sequence matches the first follicular map FM1 best. Thus, the location of the second follicular map FM2-2 of the sequence matches that of the first follicular map FM1 best, and a reliable analysis result may be determined from the second follicular map FM2-2 of the sequence of second follicular map, the first follicular map FM1, and, in embodiments, the second videodermoscopy image IM2-2 of the sequence of second videodermoscopy images and the first videodermoscopy image IM1.

The use of a sequence of second videodermoscopy images IM2-1, IM2-2, IM2-3 and matching a prior first follicular map FM1 with the second follicular maps FM2-1, FM2-2, FM2-3 allows to refrain from micro-tattoos as reference symbols applied to the skin to allow imaging roughly the same skin area at different moments in time. This may give some cosmetic and physical relief to persons subject to a hair condition or skin condition monitoring or treatment. Further, some countries do not allow micro-tattoos, e.g. because they are considered to violate a person's physical integrity; some countries do not allow them at all, and other countries not for cosmetic purposes. The system presented here may therefore provide a virtual tattoo, where the first follicular map FM1 acts as a robust reference for identifying a position on a person's skin, and, optionally, also as an identification of the person. Hereby, a high-quality analysis result can be obtained.

In an embodiment, the analysis unit is arranged to provide a feedback signal indicative of the quality of the match between the first follicular map FM1 and the sequence of the second follicular maps, thereby allowing a person or another system to react on the signal. In a further embodiment, the virtual tattoo is used real-time and the analysis unit provides a feedback signal to a person operating the camera once the analysis unit detects that there is a match between the first follicular map FM1 and one of the second follicular maps of the sequence FM2-SEQ. This allows the person to more precisely position the camera under guidance of the analysis unit's feedback signal to find an optimally matching area. The virtual tattoo may thus provide a position on a person's skin.

Figure 9:
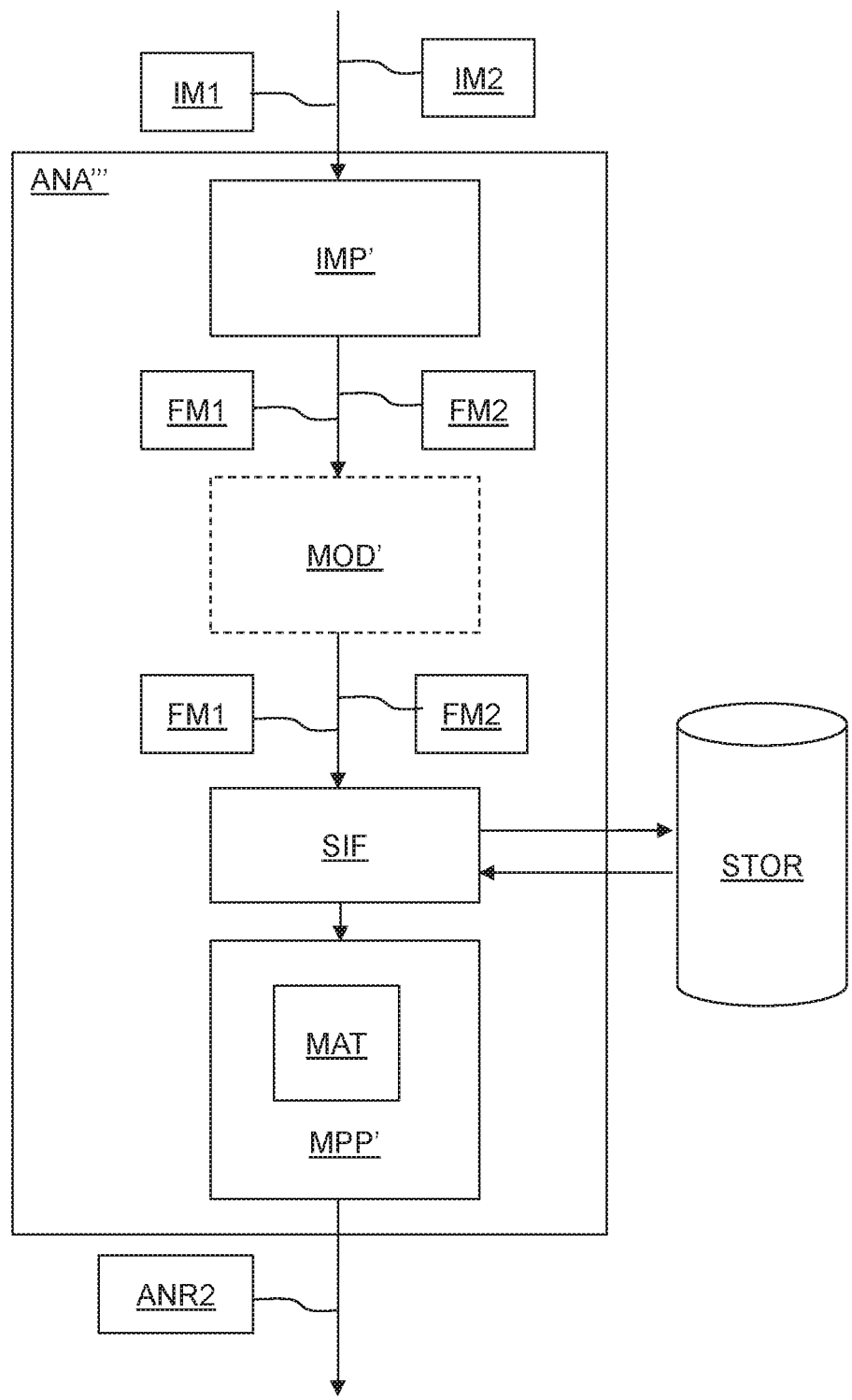

FIG. 9 shows another analysis unit ANA''' for assessment of hair condition according to another embodiment. The analysis unit ANA''' shown in FIG. 6 differs from the analysis unit ANA'' shown in FIG. 4 in that the analysis unit ANA''' further comprises a storage interface unit SIF arranged to cooperate with a storage unit STOR. Storage unit STOR is shown to be external to the analysis unit ANA''', but may in alternative embodiments ne an integral part of analysis unit ANA'''. Storage unit STOR may be a cloud device, and may as such be connected to the analysis unit ANA''' permanently or only when the analysis unit ANA''' connects to the storage unit STOR. The storage interface unit SIF is arranged to store the follicular maps FM1, FM2, and optionally the videodermoscopy images IM1, IM2, in the storage unit STOR after the follicular maps FM1, FM2 have been obtained from the image processor IMP' or the map modification unit MOD. The storage interface unit SIF is further arranged to retrieve the follicular maps FM1, FM2, and optionally the videodermoscopy images IM1, IM2, from the storage unit STOR for analysis.

Figure 10:
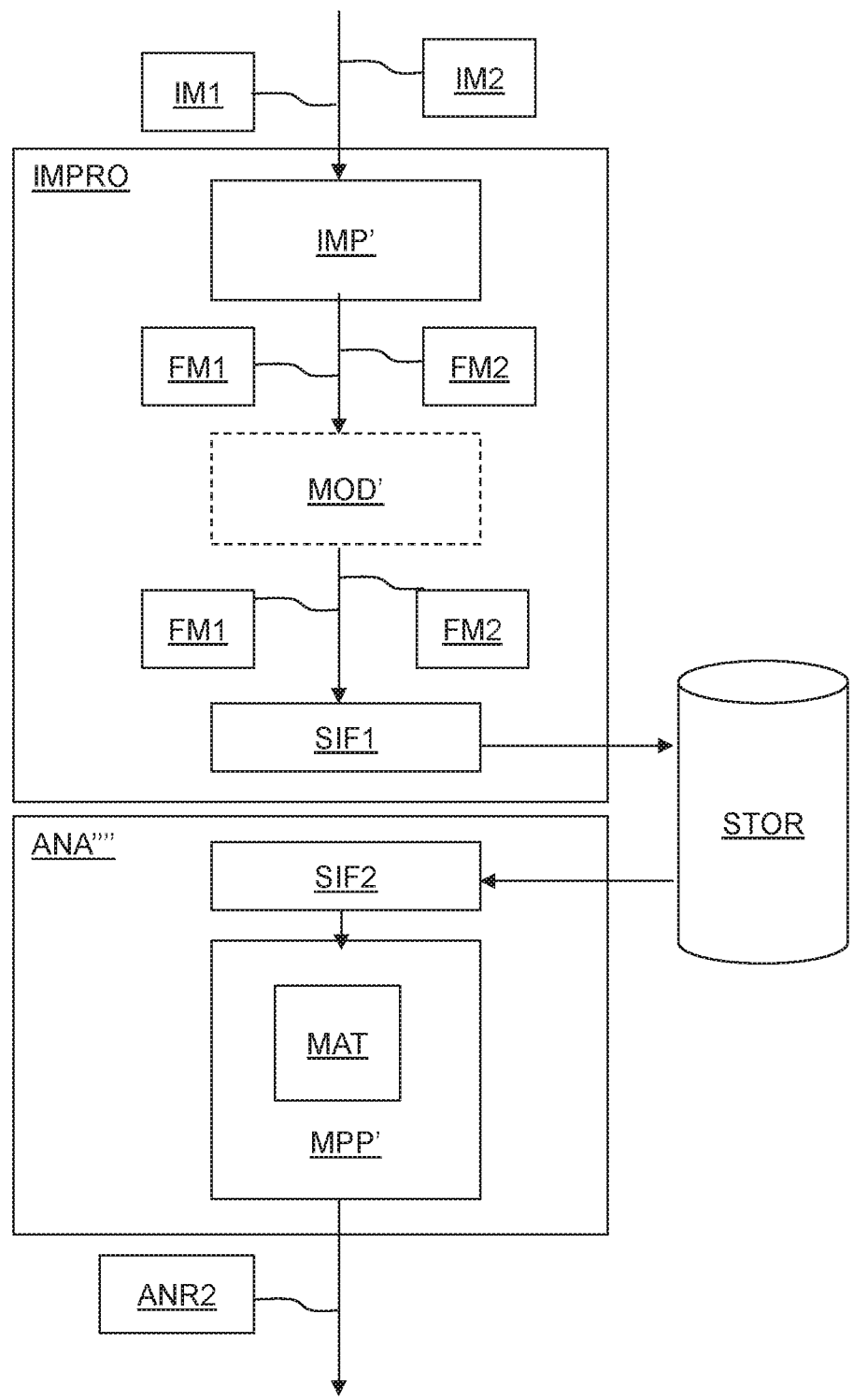

FIG. 10 shows another analysis unit ANA'''' for assessment of hair condition according to another embodiment. The analysis unit ANA''' shown in FIG. 10 differs from the analysis unit ANA''' shown in FIG. 9 in that the analysis unit ANA'''' does not comprise the image processor IMP' and the map modification unit MOD. The image processor IMP' and the map modification unit MOD' are instead provided as part of a separate unit shown as image provided IMPRO. The image provider IMPRO further comprises a first storage interface unit SIF1 arranged to cooperate with a storage unit STOR. Storage unit STOR may be a cloud device, and may as such be connected to the image provider IMPRO and the analysis unit ANA''' permanently or only when image provider IMPRO or the analysis unit ANA''' connects to the storage unit STOR. The storage interface unit SIF is arranged to store the follicular maps FM1, FM2, and optionally the videodermoscopy images IM1, IM2, in the storage unit STOR after the follicular maps FM1, FM2 have been obtained from the image processor IMP'. The analysis unit ANA'''' comprises a second storage interface unit SIF2 arranged to cooperate with the storage unit STOR. The second storage interface unit SIF2 is arranged to retrieve the follicular maps FM1, FM2, and optionally the videodermoscopy images IM1, IM2, from the storage unit STOR for analysis.

Figure 11:
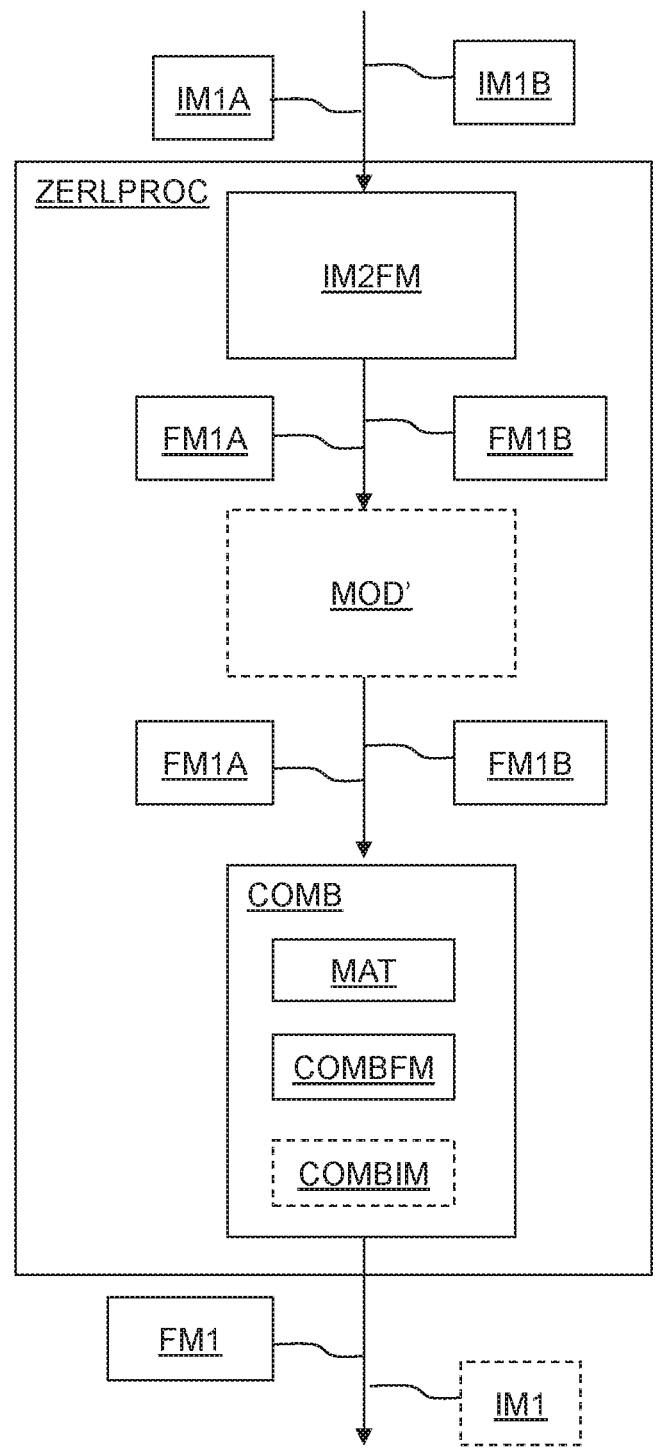

FIG. 11 shows a zero-loss processor ZERLPROC according to an embodiment. The zero-loss processor ZERLPROC is arranged to receive a plurality of first videodermoscopy input images IM1A, IM1B. The plurality of first videodermoscopy input images IM1A, IM1B is obtained from taking a sequence of videodermoscopy images at short time intervals, e.g. seconds or minutes apart while rearranging the camera or the hair in between successive images. The hair may e.g. be non-combed and combed, combed in different directions—one may observe differences in hair direction between figure IM1A and IM1B-, parted or otherwise rearranged in a suitable manner. The camera may e.g. be shifted a small distance, e.g., 1-10 mm, between successive images.

The camera may be a digital still camera. The camera may alternatively be a video camera arranged to provide a sequence of video images, a successive sequence of video images or a sub-set of successive video images providing the plurality of first videodermoscopy input images.

The zero-loss processor ZERLPROC comprises an input image processor IM2FM arranged to perform an image processing algorithm on each of the first videodermoscopy input images IMA1, IMA2 of the plurality of first videodermoscopy input images IM1A, IM1B to generate a plurality of first follicular maps FM1A, FM1B, each first follicular map representing a first plurality of hair root positions in the corresponding first videodermoscopy input image.

The zero-loss processor ZERLPROC comprises a combiner COMB. The combiner COMB comprises a matching unit MAT, a follicular map combiner COMBFM. In further embodiments, the combiner COMB may further comprise an input image combiner COMBIM.

The matching unit MAT in the embodiment shown in FIG. 11 may correspond to the matching unit MAT described with reference to FIG. 4. The matching unit MAT in the embodiment shown in FIG. 11 may be arranged to at least relate hair root positions in a second map FM1B of the plurality of first follicular maps to hair root positions of the first map FM1A in at least a common skin area to determine a plurality of related hair root positions. Each related hair root position of a hair root in the second map FM1B may thus be related to a hair root position in the first map FM1A of the same hair root. This may be performed as part of determining the common skin area, or after the common skin are has been determined. Reference is further made to the description of the matching unit MAT with reference to FIG. 4. As shown, the matching unit may determine a transformation function TF12 which relates hair root positions in the first map FM1A of the plurality of first follicular maps FM1A, FM1B to hair root positions of the same hair in the second map FM1B. Just for illustration and in order to not obscure the Figure, the size, shape and position of the input images are drawn to reflect the same complete common skin area in FIG. 12.

The combiner COMB shown in FIG. 11 is arranged to obtain the plurality of first follicular maps FM1A, FM1A from the input image processor IM2FM. The combiner COMB may further be arranged to obtain the plurality of first videodermoscopy input images IM1A, IM1B from the input image processor. The follicular map combiner COMBFM is arranged to determine a combined first follicular map FM1 from the plurality of first follicular maps FM1A, FM1A. The input image combiner COMBIM is, in further embodiments, arranged to determine a combined input image IM1 from plurality of first videodermoscopy input images IM1A, IM1B using the plurality of first follicular maps FM1A, FM1A.

The zero-loss processor ZERLPROC may be arranged to output the combined first follicular map FM1, which may be used as the first or second follicular map in the embodiments described above with reference to FIG. 1-FIG. 10. In further embodiments, the zero-loss processor ZERLPROC may be arranged to output the combined input image IM1, which may be used as the first or second videodermoscopy image in the embodiments described above with reference to FIG. 1-FIG. 10.

Similar to analysis unit ANA' shown in FIG. 2, the zero-loss processor ZELFPROC may comprise a map modification unit MOD', similar to the one described with reference to FIG. 4. In such embodiment, the input image processor IM2FM is arranged to, as part of obtaining the plurality of first follicular maps FM1A, FM1B, cooperate with the map modification unit MOD'. The map modification unit MOD' is arranged to present the plurality of first follicular maps FM1A, FM1B as obtained from the performing of the image processing algorithm on the plurality of first videodermoscopy input images to a human assistant, and to allow the human assistant to review the plurality of first follicular maps FM1A, FM1B and to modify the first follicular maps FM1A, FM1B such as to, at least, add and/or remove one or more hair root positions from the first follicular maps FM1A, FM1B. The plurality of first follicular maps as reviewed and modified is thereafter used for combining the plurality of first follicular maps FM1A, FM1B and, in embodiments, the plurality of first videodermoscopy input images IM1A, IM1B. The quality of the plurality of first videodermoscopy input images may hereby be improved, as human assistants may be able to identify false positive and or false negatives and may be able to correct errors made by the hardware of the system.

The zero-loss processor ZERLPROC may be used as an alternative to image processor IMP. The zero-loss processor ZERLPROC may be used in an alternative embodiment of image processor IMP'.

Figure 12:
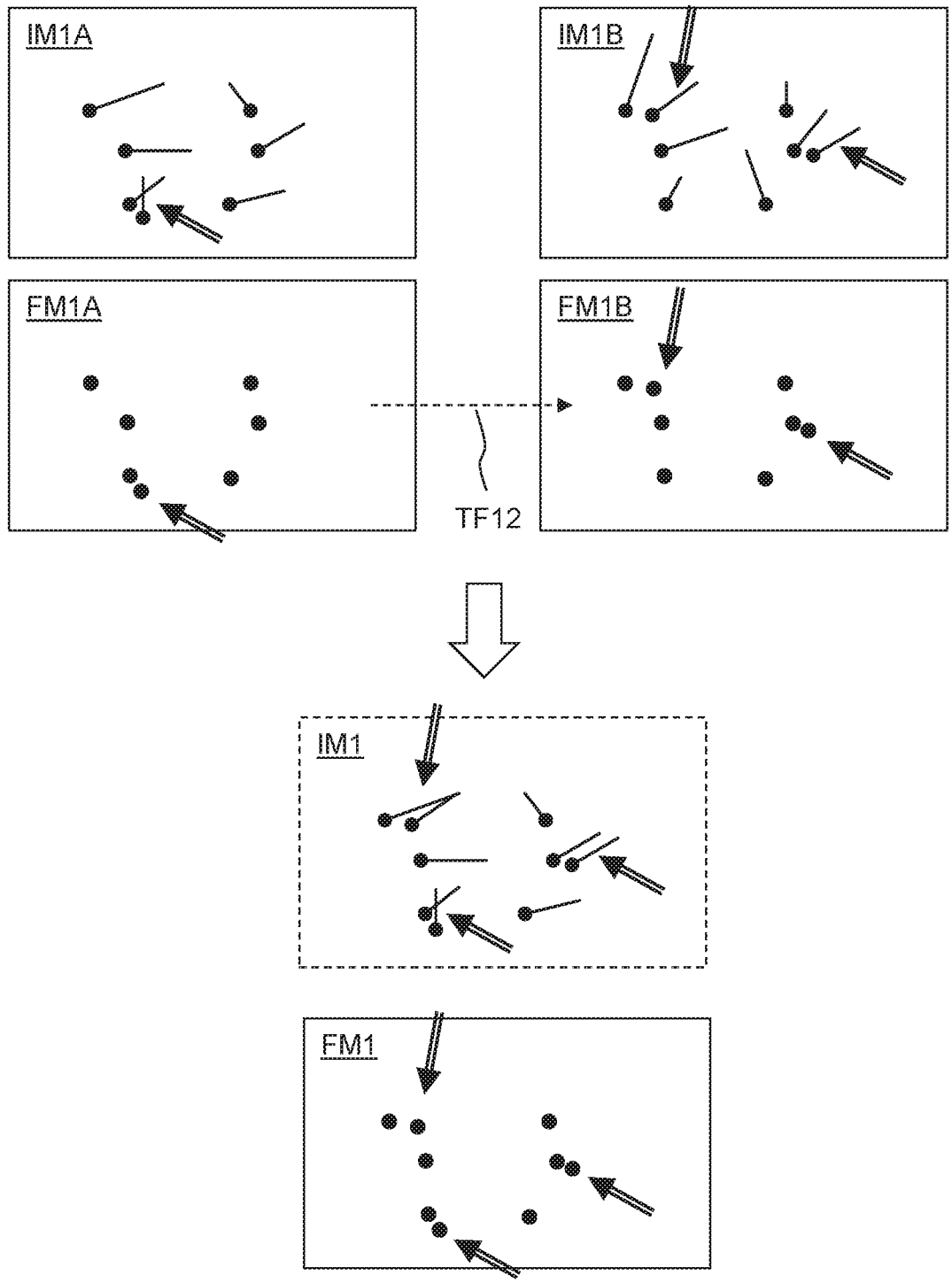

FIG. 12 schematically shows examples of videodermoscopic images and follicular maps to illustrate the operation of a zero-loss processor of FIG. 11, in particular of the operation of the combiner COMB. FIG. 12 schematically shows two input images IM1A, IM1B of a plurality of first videodermoscopy input images IM1A, IM1B. The two input images schematically represent two images of substantially the same skin part taken a few seconds—e.g., 5 seconds—apart with the hair having been combined in the meantime. FIG. 12 also schematically shows two maps FM1A, FM2A of a plurality of first follicular maps FM1A, FM1A, each reflecting the plurality of hair root positions in the corresponding first videodermoscopy input images IM1A, IM1B.

It may be observed in FIG. 12 that the first input image IM1A and the second input IM1B of substantially the same skin part show—apart from differences in direction of some of the hairs—three differences, indicated by double arrows: the first input image IM1A shows a hair in the bottom left quadrant that is not visible in the second input image IM1B, and the associated hair root position is also present in first map FM1A but absent in second map M1B. Similarly, another two hairs are visible in the second input image IM1B that are not visible in first input image 1A, and similarly for the two associated hair root positions that are in second map FM1B but not in first map FM1A.

As the two maps FM1A and FM1B are matched by the matching unit MAT such that the positions of individual hair appearing in both maps are known, the combiner COMB is arranged to identify which hair root positions in first map FM1A do not appear in second map FM1B and vice versa. Adding the hair root positions that do not appear in first map FM1A but that do appear in second map FM1B to the hair root positions in first map FM1A may thus provide a combined first follicular map FM1. The follicular map combiner COMBFM may thus be arranged to determine a combined first follicular map FM1 from the plurality of first follicular maps FM1A, FM1A. Likewise, adding from the second input image IM1B the hair that relates to hair root positions that do not appear in first map FM1A but that do appear in second map FM1B to the first input image IM1A may thus provide a combined input image IM1. The input image combiner COMBIM may thus be arranged to determine a combined input image IM1 from plurality of first videodermoscopy input images IM1A, IM1B using the plurality of first follicular maps FM1A, FM1A.

Creating a combined first follicular map FM1 from a plurality of first videodermoscopy input images and/or creating a combined input image IM1 from plurality of first videodermoscopy input images results in, respectively, a follicular map and/or a videodermoscopy image with an increased detection efficiency of hair root positions and/or hair. When combined with any of the other embodiments described, this may result in a more precise and/or more reliable and/or more consistent analysis result.

Figure 13:
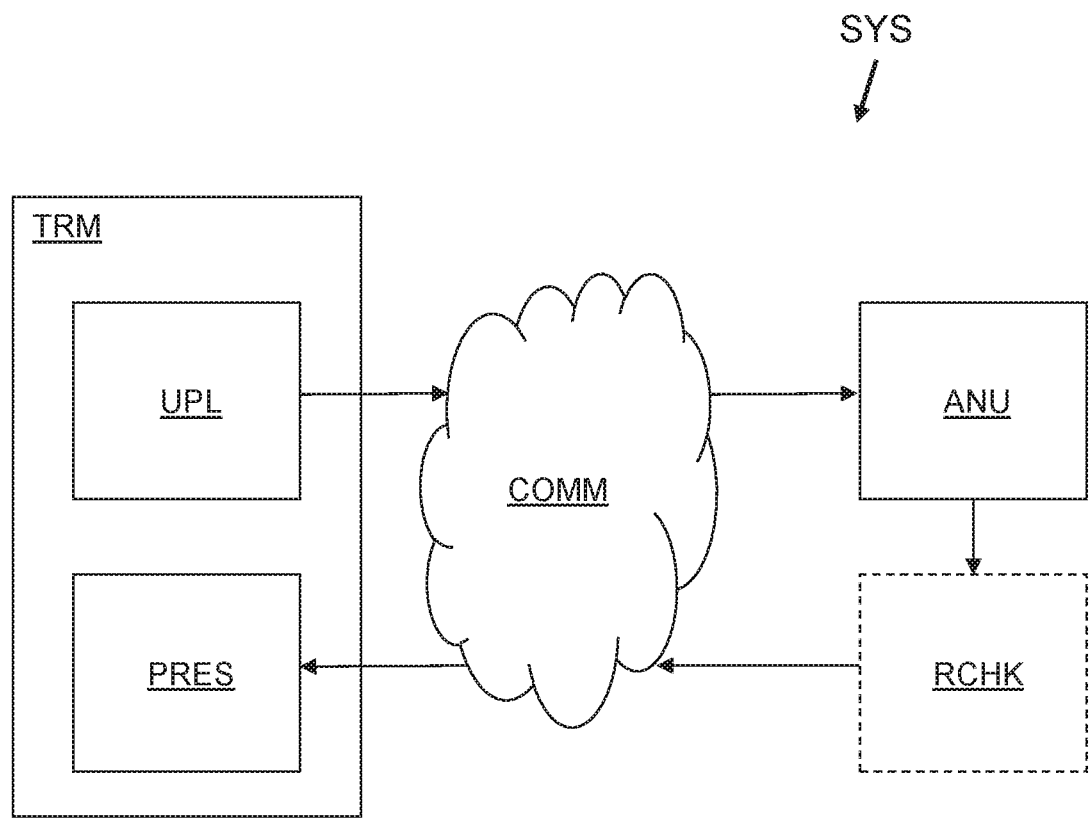

FIG. 13 schematically shows a system SYS for assessment of hair condition. The system SYS comprises an upload unit UPL, an analysis unit ANU, and a presentation unit PRES. The upload unit UPL is arranged to receive one or more videodermoscopy images, e.g. from a dermatologist or an assistant thereof that registered the videodermoscopy images on a scalp from a patient, e.g. by feeding into a scanner, by retrieving from a storage for example at the dematologists'clinic, or by retrieving from a communication network. The one or more videodermoscopy images comprise at least the first videodermoscopy image. The upload unit UPL is further arranged to upload the one or more videodermoscopy images to the analysis unit, for example via a communication network, or via e-mail, or as a hardcopy via surface mail or a delivery service. The analysis unit ANU is arranged to receive the one or more videodermoscopy images from the upload unit UPL. The analysis unit ANU is arranged to obtain a videodermoscopic analysis result from the one or more videodermoscopy images. The videodermoscopic analysis result comprises at least one of the analysis result suitable for assessment of hair condition as obtained by one of the analysis units described with reference to FIG. 1-FIG. 10, and an examination result derived from the analysis result result. The presentation unit PRES is arranged to receive the videodermoscopic analysis result from the analysis unit ANU and to present at least part of the analysis result to a user. The presentation unit PRES may be arranged to present at least part of the analysis result to a user on, for example, a display, on paper, in a computer-readable data format, in a human-readable form or on a data storage medium, in a qualitative or quantitative manner, as a graphical or textual, such as table or phrases, representation. The user may, e.g., be a patient, a general practitioner, a dermatology nurse, a dermatologist, or a scientist.

FIG. 13 shows that the system SYS may further comprise a result check unit RCHK. The result check unit RCHK is arranged to receive the videodermoscopic analysis result from the analysis unit ANU. The result check unit RCHK is arranged to review the videodermoscopic analysis result and to modify the videodermoscopic analysis result. For example, the videodermoscopic analysis result may be changed, supplemented, summarized or reformatted. The videodermoscopic analysis result may e.g. be supplemented with a diagnosis of a hair disorder, a treatment proposal or a treatment change. E.g., an expert system or a human expert dermatologist may draw a diagnosis as the presence, or lack of presence, of AGA. The result check unit RCHK is arranged to provide the videodermoscopic analysis result as modified to the presentation unit to allow the presentation unit to present at least part of the videodermoscopic analysis result as modified to the user. The result check unit RCHK may be connected to the analysis unit ANU via a communication network such as the internet, whereby the result check and the image processing may take place at different geographical locations. The result check unit RCHK may alternatively be directly connected to the analysis unit ANU and part of a single unit, e.g., the analysis unit ANU and the result check unit RCHK may be implemented in a personal computer of a dermatologist.

As shown in FIG. 13, the upload unit UPL may be connected to the analysis unit ANU via a communication network COMM. The communication network COMM may be a virtual private network. The communication network COMM may be the Internet. Hereby, videodermoscopic images registered at various places, e.g. at various dermatologic clinics, may be sent via the internet to the analysis unit ANU at a centralized location, at which centralized location a consistent and quality-controlled processing may be performed to obtain the follicular maps and the analysis results. The processing at the centralized location simplifies the use of a pool of well-trained staff to do the review and modification of the follicular maps described above with reference to the map modification unit MOD.

As shown in FIG. 13, the presentation unit PRES may be connected to the analysis unit ANU via a communication network. The communication network may be the same virtual private network, another virtual private network, or, for example, the Internet. The analysis unit ANU may thus be at a central location, and the presentation unit PRES may be at a general practitioner, a nurse, a patient, or elsewhere.

In embodiments, the system SYS comprises a user terminal TERM. The user terminal TERM comprises the upload unit UPL and the presentation unit PRES. The user terminal TERM is connected to the analysis unit ANU via a communication network COMM. The user terminal TERM may, e.g., be a computer at a dermatologist's clinic that can connect via the internet, e.g. using a virtual private network, to the analysing unit ANU at a centralized location.

Figure 14:
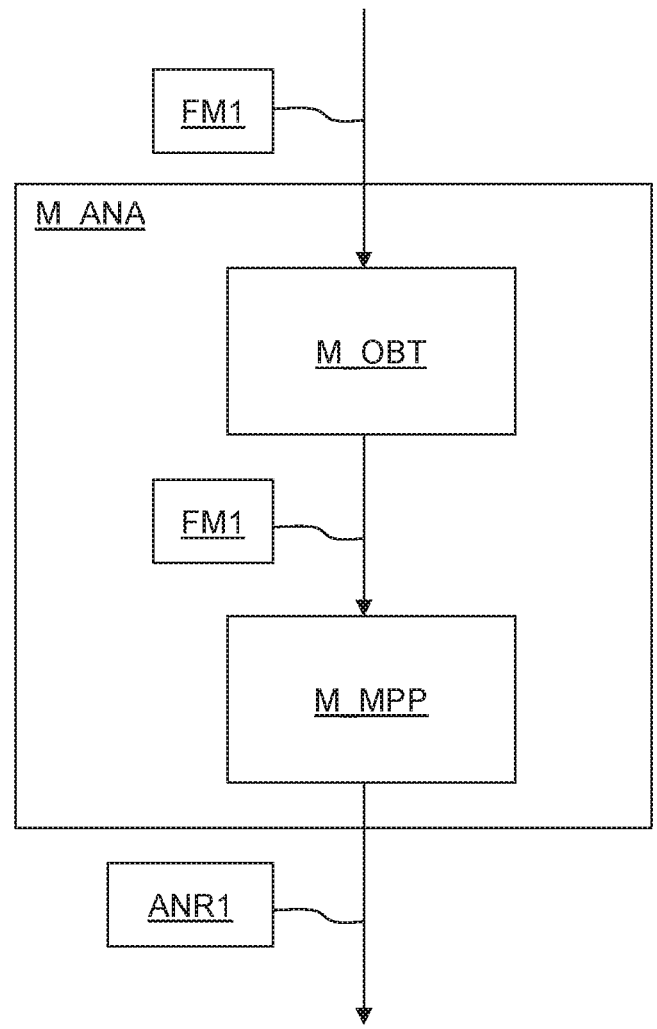

FIG. 14 schematically shows a method M_ANA for assessment of hair condition according to an embodiment. The method M_ANA comprises obtaining OBT a first follicular map FM1 representing a first plurality of hair root positions in a first videodermoscopy image. The method M_ANA comprises analysing M_MPP at least the first follicular map to determine an analysis result ANR1 suitable for assessment of hair condition. Reference is further made to FIG. 1.

Figure 15:
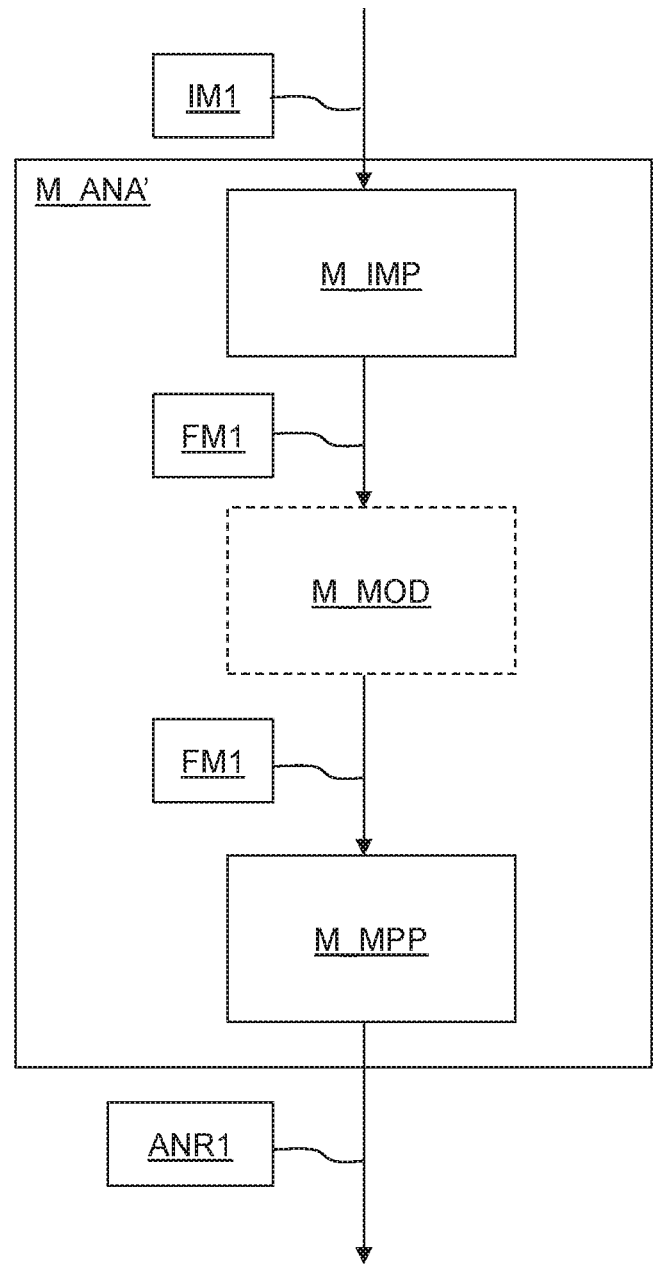

FIG. 15 schematically shows a method M_ANA' for assessment of hair condition according to a further embodiment. The method M_ANA' comprises performing M_IMP an image processing algorithm on a first videodermoscopy image IM1 to obtain a first follicular map FM1 representing a first plurality of hair root positions in the first videodermoscopy image. The method M_ANA' further comprises analysing M_MPP at least the first follicular map to determine an analysis result ANR1 suitable for assessment of hair condition. The method M_ANA' may further comprise a present-and-modify option M_MOD comprising presenting the first follicular map as obtained from the performing of the image processing algorithm on the first videodermoscopy image to a human assistant, and allow the human assistant to review the first follicular map and to modify the first follicular map such as to, at least, add and/or remove one or more hair root positions from the first follicular map.

Figure 16:
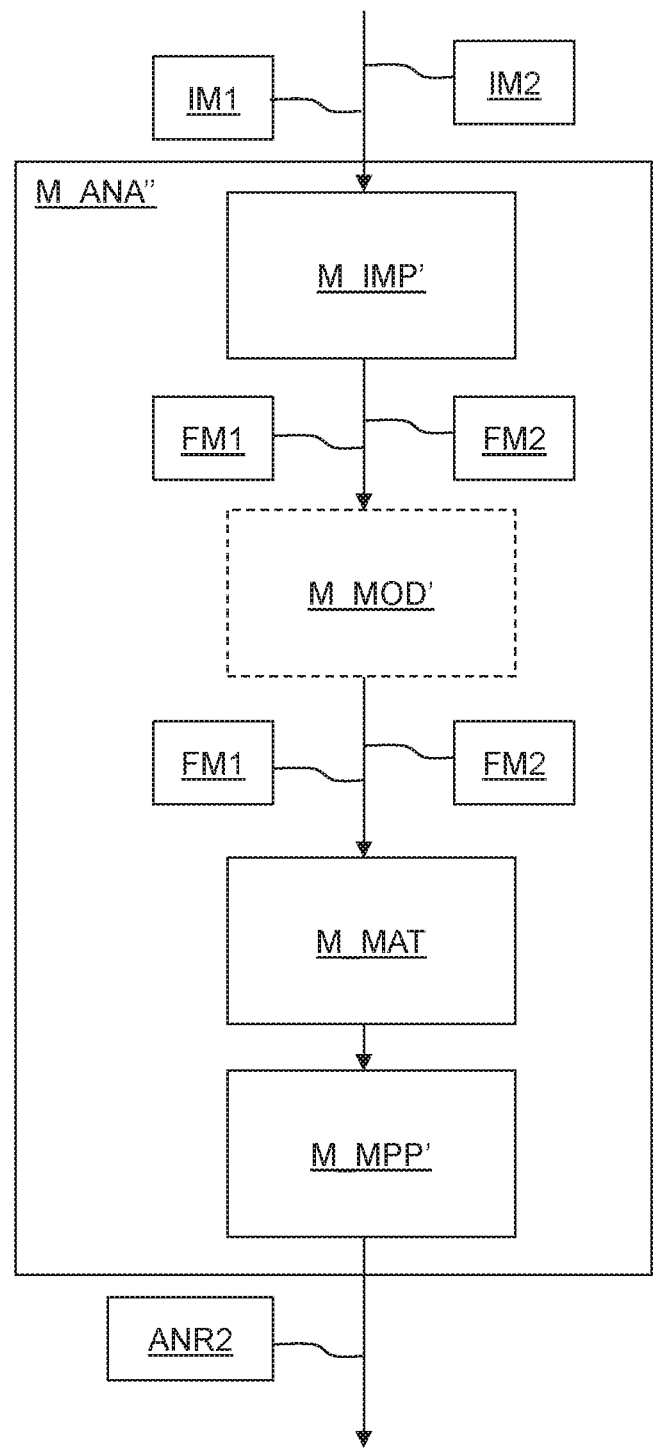

FIG. 16 schematically shows a method M_ANA" for assessment of hair condition according to again a further embodiment. The method M_ANA''' comprises performing M_IMP' an image processing algorithm on a first videodermoscopy image IM1 to obtain a first follicular map FM1 representing a first plurality of hair root positions in the first videodermoscopy image and performing M_IMP' an image processing algorithm on a second videodermoscopy image to obtain the second follicular map representing the second plurality of hair root positions in the first videodermoscopy image to obtain FM2 a second follicular map representing a second plurality of hair root positions in a second videodermoscopy image. The method M_ANA''' may further comprise a present-and-modify option M_MOD' comprising presenting the first follicular map as obtained from the performing of the image processing algorithm on the first videodermoscopy image to a human assistant, and allow the human assistant to review the first follicular map and to modify the first follicular map such as to, at least, add and/or remove one or more hair root positions from the first follicular map, and presenting the second follicular map as obtained from the performing of the image processing algorithm on the second videodermoscopy image to a human assistant, and allow the human assistant to review the second follicular map and to modify the second follicular map such as to, at least, add and/or remove one or more hair root positions from second first follicular map. The method M_ANA''' may comprises determining a common skin area from the first follicular map FM1 and the second follicular map FM2.

The method may comprise uploading one or more videodermoscopy images to an analysis unit via a communication network, for letting the analysis unit perform the method according to any one of the embodiments above, and receiving the videodermoscopic analysis result from the analysis via the communication network.

In a further embodiment, the method comprises obtaining a sequence of second follicular maps, each second follicular map representing a second plurality of hair root positions in an associated second videodermoscopy image of a corresponding sequence of different second videodermoscopy images, and determining a common skin area from the first follicular map and at least one of the second follicular maps of the sequence of second follicular maps. The first follicular map may thus effectively act as a location reference, and could be considered to function as a virtual tattoo. With this embodiment, the method may not just be arranged for determining an analysis result suitable for assessment of hair condition, but the method may additionally or alternatively be arranged for determining an analysis result suitable for assessment of skin condition.

The method may further comprise receiving one or more videodermoscopy images by an upload unit, uploading the one or more videodermoscopy images from the upload unit to an analysis unit via a communication network, for letting the analysis unit perform the method, and presenting at least part of the videodermoscopic analysis result to a user.

Figure 17:
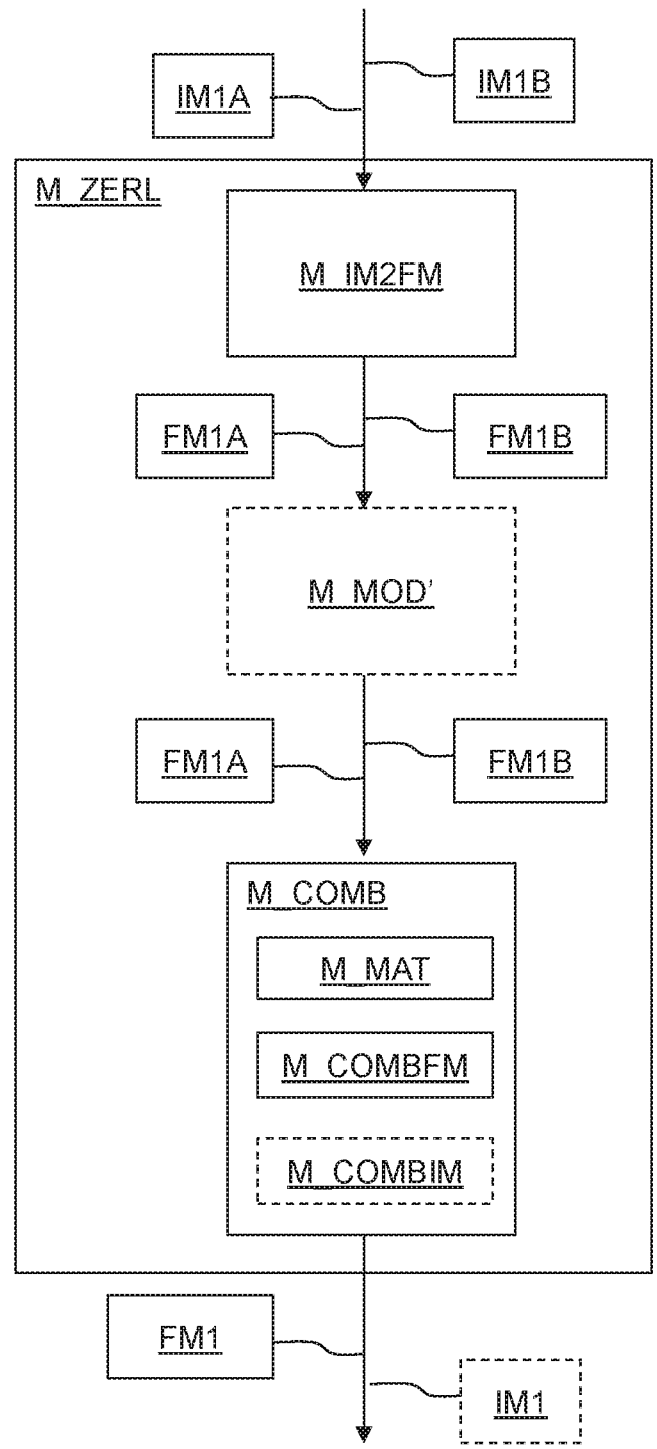

FIG. 17 schematically shows a method of zero-loss videodermoscopic image processing M-ZERL according to an embodiment. The method may further be referred to as zero-loss method M_ZERL.

The zero-loss method M_ZERL comprises receiving a plurality of first videodermoscopy input images IM1A, IM1B. The plurality of first videodermoscopy input images IM1A, IM1B is obtained from taking a sequence of videodermoscopy images at short time intervals, e.g. seconds or minutes apart while rearranging the camera or the hair in between successive images. The hair may e.g. be non-combed and combed, combed in different directions, parted or otherwise rearranged in a suitable manner. The camera may e.g. be shifted a small distance, e.g., 1-10 mm, between successive images. The camera may be a digital still camera. The camera may alternatively be a video camera arranged to provide a sequence of video images, a successive sequence of video images or a sub-set of successive video images providing the plurality of first videodermoscopy input images.

The zero-loss method M_ZERL comprises performing an image processing algorithm on each of the first videodermoscopy input images IMA1, IMA2 of the plurality of first videodermoscopy input images IM1A, IM1B to generate a plurality of first follicular maps FM1A, FM1 B, each first follicular map representing a first plurality of hair root positions in the corresponding first videodermoscopy input image.

The zero-loss method M_ZERL comprises relating M_MAT hair root positions in a second map FM1 B of the plurality of first follicular maps to hair root positions of the first map FM1A in at least a common skin area to determine a plurality of related hair root positions. Each related hair root position of a hair root in the second map FM1 B may thus be related to a hair root position in the first map FM1A of the same hair root. This may be performed as part of determining the common skin area, or after the common skin area has been determined. Reference is further made to the description of the matching unit MAT with reference to FIG. 4.

The zero-loss method M_ZERL comprises determining M_COMBFM a combined first follicular map FM1 from the plurality of first follicular maps FM1A, FM1A.

The zero-loss method M_ZERL may further comprise determining M_COMBIM a combined input image IM1 from the plurality of first videodermoscopy input images IM1A, IM1B using the plurality of first follicular maps FM1A, FM1A.

The zero-loss method M_ZERL may further comprise outputting the combined first follicular map FM1. The zero-loss method M_ZERL may comprise outputting the combined first follicular map FM1 for use as the first or second follicular map in any one of the embodiments described above with reference to FIG. 1-FIG. 16.

The zero-loss method M_ZERL may further comprise outputting the combined input image IM1. The zero-loss method M_ZERL may further comprise outputting the combined input image IM1 for use as the first or second videodermoscopy image in any one of the embodiments described above with reference to FIG. 1-FIG. 16.

The zero-loss method M_ZERL may further comprise a present-and-modify option M_MOD' comprising presenting the plurality of first follicular maps FM1A, FM1 B as obtained from the performing of the image processing algorithm on the plurality of first videodermoscopy input images IM1A, IM1 B to a human assistant, and allow the human assistant to review the plurality of first follicular maps FM1A, FM1 B and to modify the first follicular maps FM1A, FM1 B such as to, at least, add and/or remove one or more hair root positions from the first follicular maps FM1A, FM1 B. The plurality of first second follicular maps as reviewed and modified is thereafter used for combining the plurality of first follicular maps FM1A, FM1 B and, in embodiments, the plurality of first videodermoscopy input images IM1A, IM1 B.

Figure 18:
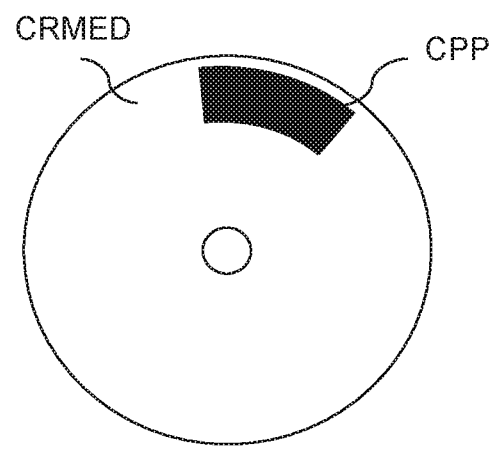
FIG. 18 shows a computer readable medium comprising a computer program product.

FIG. 18 shows a computer readable medium CRMED comprising a computer program product CPP, the computer program product CPP comprising instructions for causing a processor apparatus to perform a method according to any one embodiment or a part of thereof. The computer program product CPP may be embodied on the computer readable medium CRMED as physical marks or by means of magnetization of the computer readable medium CPP. However, any other suitable embodiment is conceivable as well.

Furthermore, it will be appreciated that, although the computer readable medium CRMED is shown in FIG. 18 as an optical disc, the computer readable medium CRMED may be any suitable computer readable medium, such as a hard disk, solid state memory, flash memory, etc., and may be non-recordable or recordable. The computer program product CPP may thus comprise a computer program comprising instructions arranged to, when executed by a computer, execute at least part of the method of any one of the embodiments described above.

It should be noted that the above-mentioned embodiments illustrate rather than limit the invention, and that those skilled in the art will be able to design many alternative embodiments.

The invention may also be implemented in a computer program for running on a computer system, at least including code portions for performing steps of a method according to the invention when run on a programmable apparatus, such as a computer system or enabling a programmable apparatus to perform functions of a device or system according to the invention. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. The computer program may be provided on a data carrier, such as a CD-type optical disc, a DVD-type optical disc, a hard disk, or diskette, stored with data loadable in a memory of a computer system, the data representing the computer program. The data carrier may thus be a tangible data carrier. The data carrier may be a data connection, such as a telephone cable or a network cable. The data carrier may further be a non-tangible data carrier such as a wireless connection.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An analysis unit for assessment of hair condition, the analysis unit comprising a map processor, the map processor being configured to:
   obtain a first follicular map representing a first plurality of hair root positions in a first videodermoscopy image,
   obtain a second follicular map representing a second plurality of hair root positions in a second videodermoscopy image,
   determine a common skin area from the first follicular map and the second follicular map,
   relate hair root positions in the second follicular map to hair root positions of the first follicular map in the common skin area to determine a plurality of related hair root positions, each related hair root position of a hair root in the second follicular map being related to a hair root position in the first follicular map of the same hair root, and compare a change in condition of individual hair between the first and second videodermoscopy image to determine the analysis result suitable for assessment of hair condition.

2. The analysis unit according to claim 1, the analysis unit further comprising an image processor, wherein:
the image processor being configured to perform an image processing algorithm on a first videodermoscopy image to generate the first follicular map representing the first plurality of hair root positions in the first videodermoscopy image, and
the map processor being configured to obtain the first follicular map from the image processor.

3. The analysis unit according to claim 2, the image processor further being configured to perform the image processing algorithm on a second videodermoscopy image to generate the second follicular map representing the second plurality of hair root positions in the second videodermoscopy image, and
the map processor being configured to obtain the second follicular map from the image processor.

4. The analysis unit according to claim 2, the image processor being configured to, as part of obtaining the first follicular map, cooperate with a map modification unit, the map modification unit being configured to:
present the first follicular map as obtained from the performing of the image processing algorithm on the first videodermoscopy image to a human assistant, and
allow the human assistant to review the first follicular map and to modify the first follicular map such as to, at least, add and/or remove one or more hair root positions from the first follicular map.

5. The analysis unit according to claim 1, the map processor being further configured to:
obtain a sequence of second follicular maps, each second follicular map representing a second plurality of hair root positions in an associated second videodermoscopy image of a corresponding sequence of different second videodermoscopy images, and
determine the common skin area from the first follicular map and at least one of the second follicular maps of the sequence of second follicular maps.

6. The analysis unit according to claim 5, the map processor being further configured to:
analyze differences between the common skin area in the first follicular map and the common skin area in the second follicular map to determine an analysis result suitable for assessment of skin condition.

7. The analysis unit according to claim 1, the map processor being further configured to, in determining the analysis result:
identify an appearing of new hair roots in the common skin area in the second follicular map compared to the common skin area in the first follicular map, and/or
identify a disappearing of hair roots from the common skin area in the second follicular map compared to the common skin area in the first follicular map.

8. The analysis unit according to claim 1, the map processor being further configured to analyze differences between at least the common skin area in the first videodermoscopy image and the common skin area in the second videodermoscopy image to determine the analysis result suitable for assessment of hair condition.

9. The analysis unit according to claim 8, the map processor being further configured to, in analyzing differences between at least the common skin area in the first videodermoscopy image and the common skin area in the second videodermoscopy image, compare lengths of individual hair between the first videodermoscopy image captured from a part of a skin, such as part of a human scalp, before shaving and lengths of the same individual hair in a second videodermoscopy image captured from the same part after shaving as part of an examination of shaving performance on hair condition, in particular hair length.

10. The analysis unit according to claim 8, the map processor being further configured to, in analyzing differences between at least the common skin area in the first videodermoscopy image and the common skin area in the second videodermoscopy image, compare lengths of individual hairs between a first videodermoscopy image captured from a part of a skin, such as part of a human scalp, immediately after shaving and a second videodermoscopy image captured from the same part one or more days after shaving, and to calculate estimates of the lengths of individual hairs immediately after shaving from the change of lengths.

11. The analysis unit according to claim 8, the map processor being further configured to, in analyzing differences between at least the common skin area in the first videodermoscopy image and the common skin area in the second videodermoscopy image, compare presence and/or diameters and/or lengths of individual hair between the first videodermoscopy image captured from a part of a skin before epilation and presence and/or diameters and/or lengths of the same individual hair in a second videodermoscopy image captured from the same part after epilation as part of an examination of epilation performance on hair condition, in particular hair extraction, hair diameter and hair length.

12. The analysis unit according to claim 8, the map processor being further configured to, in analyzing differences between at least the common skin area in the first videodermoscopy image and the common skin area in the second videodermoscopy image, compare presence and/or diameters and/or lengths of individual hair between a first videodermoscopy image captured from a part of a skin immediately or shortly after epilation and a second videodermoscopy image captured from the same part one or more days after epilation, and to calculate estimates of the quality of epilation such as percentage of successful epilation and/or diameter and/or lengths of individual hair immediately after epilation from the change of diameters and/or lengths.

13. The analysis unit according to claim 1, the analysis unit further comprising a zero-loss processor, the zero-loss processor being configured to:
receive a plurality of first videodermoscopy input images captured as a sequence of videodermoscopy images,
perform an image processing algorithm on each of the first videodermoscopy input images of the plurality of first videodermoscopy input images to generate a plurality of first follicular maps, each first follicular map representing a first plurality of hair root positions in the corresponding first videodermoscopy input image,
relate hair root positions in a second map of the plurality of first follicular maps to hair root positions of a first map in at least a common skin area of the first map and the second map to determine a plurality of related hair root positions, and
determine a combined first follicular map from the plurality of first follicular maps.

14. The analysis unit according to claim 13, the zero-loss processor being configured to output the combined first follicular map to the image processor for use as the first or second follicular map.

15. The analysis unit according to claim 13, the zero-loss processor being configured to output the combined input image to the image processor for use as the first or second videodermoscopy image.

16. A system for assessment of hair condition, the system comprising:
an upload unit,
an analysis unit according for assessment of hair condition, the analysis unit comprising a map processor, the map processor being configured to:
obtain a first follicular map representing a first plurality of hair root positions in a first videodermoscopy image,
obtain a second follicular map representing a second plurality of hair root positions in a second videodermoscopy image,
determine a common skin area from the first follicular map and the second follicular map,
relate hair root positions in the second follicular map to hair root positions of the first follicular map in the common skin area to determine a plurality of related hair root positions, each related hair root position of a hair root in the second follicular map being related to a hair root position in the first follicular map of the same hair root, and
compare a change in condition of individual hair between the first and second videodermoscopy image to determine the analysis result suitable for assessment of hair condition, and
a presentation unit,
wherein the upload unit is configured to receive one or more videodermoscopy images, the one or more videodermoscopy images including at least the first videodermoscopy image and to upload the one or more videodermoscopy images to the analysis unit,
wherein the analysis unit is configured to receive the one or more videodermoscopy images from the upload unit and to obtain a videodermoscopic analysis result from the one or more videodermoscopy images, the videodermoscopic analysis result including at least one of:
the analysis result suitable for assessment of hair condition, and
an examination result derived from at least one of the analysis result suitable for assessment of hair condition, and
wherein the presentation unit is configured to receive the videodermoscopic analysis result from the analysis unit and to present at least part of the analysis result to a user.

17. The system according to claim 16, the system further comprising a result check unit, the result check unit being configured to:
receive the videodermoscopic analysis result from the analysis unit,
review the videodermoscopic analysis result and to modify the videodermoscopic analysis result, and
provide the videodermoscopic analysis result as modified to the presentation unit to allow the presentation unit to present at least part of the videodermoscopic analysis result as modified to the user.

18. A method for assessment of hair condition, the method comprising:
obtaining a first follicular map representing a first plurality of hair root positions in a first videodermoscopy image,
obtaining a second follicular map representing a second plurality of hair root positions in a second videodermoscopy image,
determining a common skin area from the first follicular map and the second follicular map,
relating hair root positions in the second follicular map to hair root positions of the first follicular map in the common skin area to determine a plurality of related hair root positions, each related hair root position of a hair root in the second follicular map being related to a hair root position in the first follicular map of the same hair root; and
comparing a change in condition of individual hair between the first and second videodermoscopy image to determine the analysis result suitable for assessment of hair condition.

19. The method of claim 18, the method further comprising:
performing an image processing algorithm on a first videodermoscopy image to obtain the first follicular map representing the first plurality of hair root positions in the first videodermoscopy image.

20. A non-transitory computer readable storage media having computer-executable instructions configured to, when executed by a processor, perform the steps comprising:
obtaining a first follicular map representing a first plurality of hair root positions in a first videodermoscopy image,
obtaining a second follicular map representing a second plurality of hair root positions in a second videodermoscopy image,
determining a common skin area from the first follicular map and the second follicular map,
relating hair root positions in the second follicular map to hair root positions of the first follicular map in the common skin area to determine a plurality of related hair root positions, each related hair root position of a hair root in the second follicular map being related to a hair root position in the first follicular map of the same hair root; and
comparing a change in condition of individual hair between the first and second videodermoscopy image to determine the analysis result suitable for assessment of hair condition.

* * * * *